United States Patent
Nakazawa et al.

(10) Patent No.: US 9,121,003 B2
(45) Date of Patent: Sep. 1, 2015

(54) CELL CULTURE INSTRUMENT AND CELL CULTURE METHOD USING THE SAME

(75) Inventors: Kohji Nakazawa, Kitakyushu (JP); Yusuke Sakai, Fukuoka (JP)

(73) Assignee: KITAKYUSHU FOUNDATION FOR THE ADVANCEMENT OF INDUSTRY, SCIENCE AND TECHNOLOGY, Kitakyushu-shi (JP)

( * ) Notice: Subject to any disclaimer, the term of this patent is extended or adjusted under 35 U.S.C. 154(b) by 594 days.

(21) Appl. No.: 12/733,563

(22) PCT Filed: Sep. 5, 2008

(86) PCT No.: PCT/JP2008/066084
§ 371 (c)(1),
(2), (4) Date: Mar. 9, 2010

(87) PCT Pub. No.: WO2009/034927
PCT Pub. Date: Mar. 19, 2009

(65) Prior Publication Data
US 2011/0003389 A1    Jan. 6, 2011

(30) Foreign Application Priority Data
Sep. 12, 2007   (JP) .................................. 2007-237159

(51) Int. Cl.
*C12M 1/22*   (2006.01)
*C12M 3/00*   (2006.01)
(Continued)

(52) U.S. Cl.
CPC .............. *C12M 23/12* (2013.01); *B01L 3/5085* (2013.01); *C12N 5/0606* (2013.01); *C12N 5/067* (2013.01); *B01L 2200/0668* (2013.01); *B01L 2300/0636* (2013.01); *B01L 2300/0829* (2013.01)

(58) Field of Classification Search
CPC .... C12M 23/12; C12N 5/067; B01L 13/5085; B01L 2200/0668; B01L 2300/0636; B01L 2300/0829
USPC ................................................ 435/305.2, 383
See application file for complete search history.

(56) References Cited

U.S. PATENT DOCUMENTS

| | | |
|---|---|---|
| 5,585,275 A | 12/1996 | Hudson et al. |
| 2003/0030184 A1 | 2/2003 | Kim et al. |

(Continued)

FOREIGN PATENT DOCUMENTS

| | | |
|---|---|---|
| EP | 1 806 394 A1 | 7/2007 |
| JP | A-2000-69957 | 3/2000 |

(Continued)

OTHER PUBLICATIONS

Japanese Office Action issued in Japanese Patent Application No. 2009-532166 on May 11, 2010 by the Japanese Patent Office. (with partial English-language translation).

(Continued)

*Primary Examiner* — Michael Hobbs
(74) *Attorney, Agent, or Firm* — Oliff PLC

(57) ABSTRACT

Provided is a cell culture instrument which has excellent operability while including a plurality of wells capable of holding cells. The cell culture instrument according to the present invention includes a base portion in which a well group including a plurality of first wells capable of holding cells is formed, and a frame portion vertically arranged around the well group of the base portion to form a second well being capable of holding a solution.

21 Claims, 27 Drawing Sheets

(51) Int. Cl.
*C12M 1/32* (2006.01)
*B01L 3/00* (2006.01)
*C12N 5/0735* (2010.01)
*C12N 5/071* (2010.01)

(56) References Cited

U.S. PATENT DOCUMENTS

| 2003/0036188 A1* | 2/2003 | Kim et al. ............. 435/288.4 |
| 2003/0104494 A1 | 6/2003 | Ravkin et al. |
| 2007/0053795 A1* | 3/2007 | Laugharn et al. ............. 422/99 |

FOREIGN PATENT DOCUMENTS

| JP | A-2005-27598 | 2/2005 |
| JP | A-2006-121991 | 5/2006 |
| JP | A-2006-122012 | 5/2006 |
| JP | A-2007-20486 | 2/2007 |

OTHER PUBLICATIONS

Kurosawa, "Methods for Inducing Embryoid Body Formation: In Vitro Differentiation System of Embryonic Stem Cells," Journal of Bioscience and Bioengineering, 2007, pp. 389-398, vol. 103, No. 5, The Society for Biotechnology, Japan.

Campbell, "Regulation of the membrane estrogen receptor-α: role of cell density, serum, cell passage number, and estradiol," The FASEB Journal, Dec. 2007, pp. 1917-1927, vol. 16.

Allen, "The Use of High-vol. Screening Procedure to Assess the Effects of Dietary Flavonoids on Human CYP1A1 Expression," Drug Metabolism and Disposition, 2001, pp. 1074-1079, No. 8, The American Society for Pharmacology and Experimental Therapeutics.

International Search Report cited in International Application No. PCT/JP2008/066084 issued by the International Bureau on Nov. 4, 2008.

Mar. 26, 2012 European Search Report issued in EP 08 83 0570.1.

Jul. 3, 2012 Office Action issued in Chinese Patent Application No. 200880106786.8 (with Concise Explanation of Relevance).

Mar. 29, 2013 Office Action issued in Chinese Patent Application No. 200880106786.8 (with concise explanation).

Mar. 20, 2013 Office Action issued in European Patent Application No. 08830570.1.

* cited by examiner

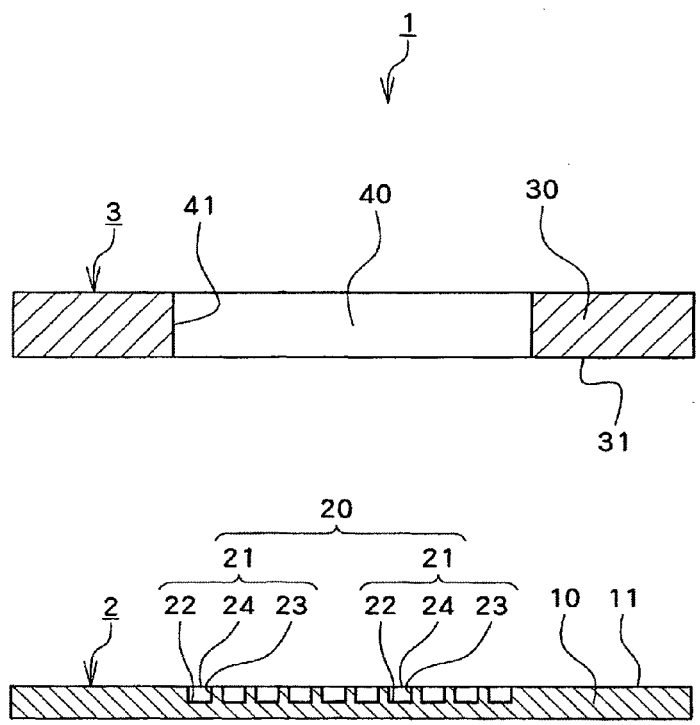
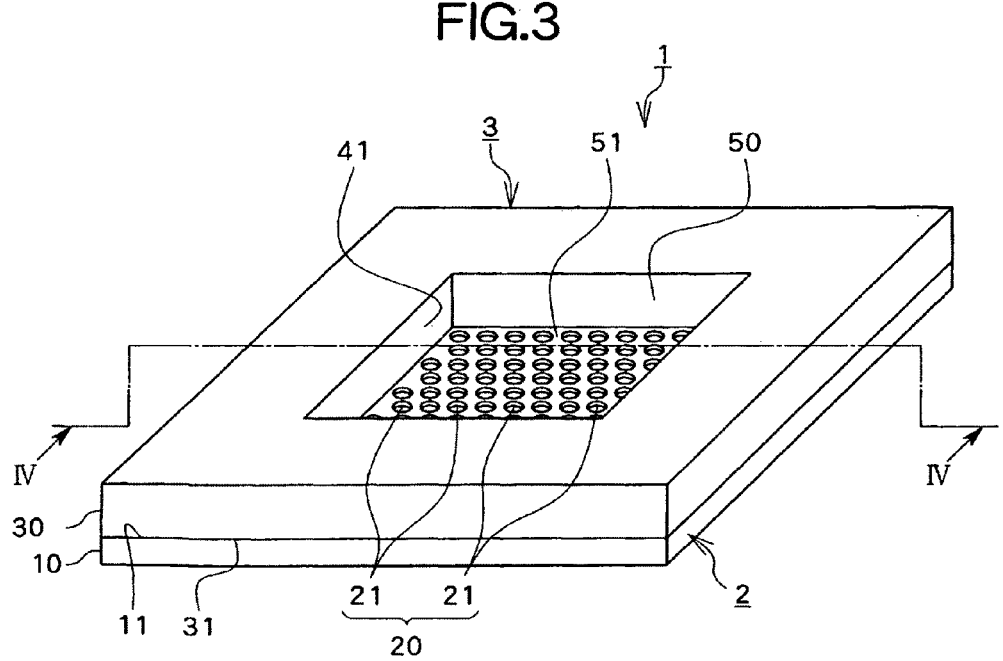

FIG.7
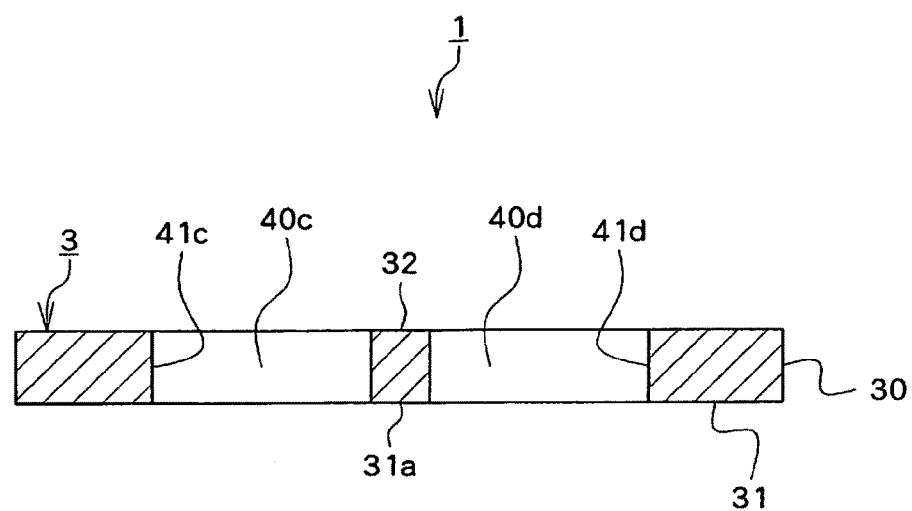
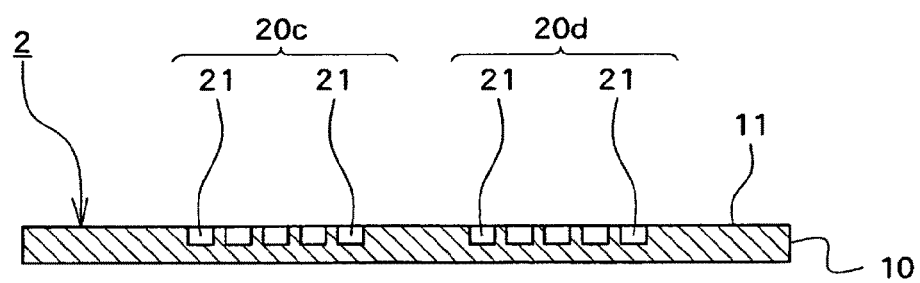

300 μm

300 μm

300 μm

300 μm

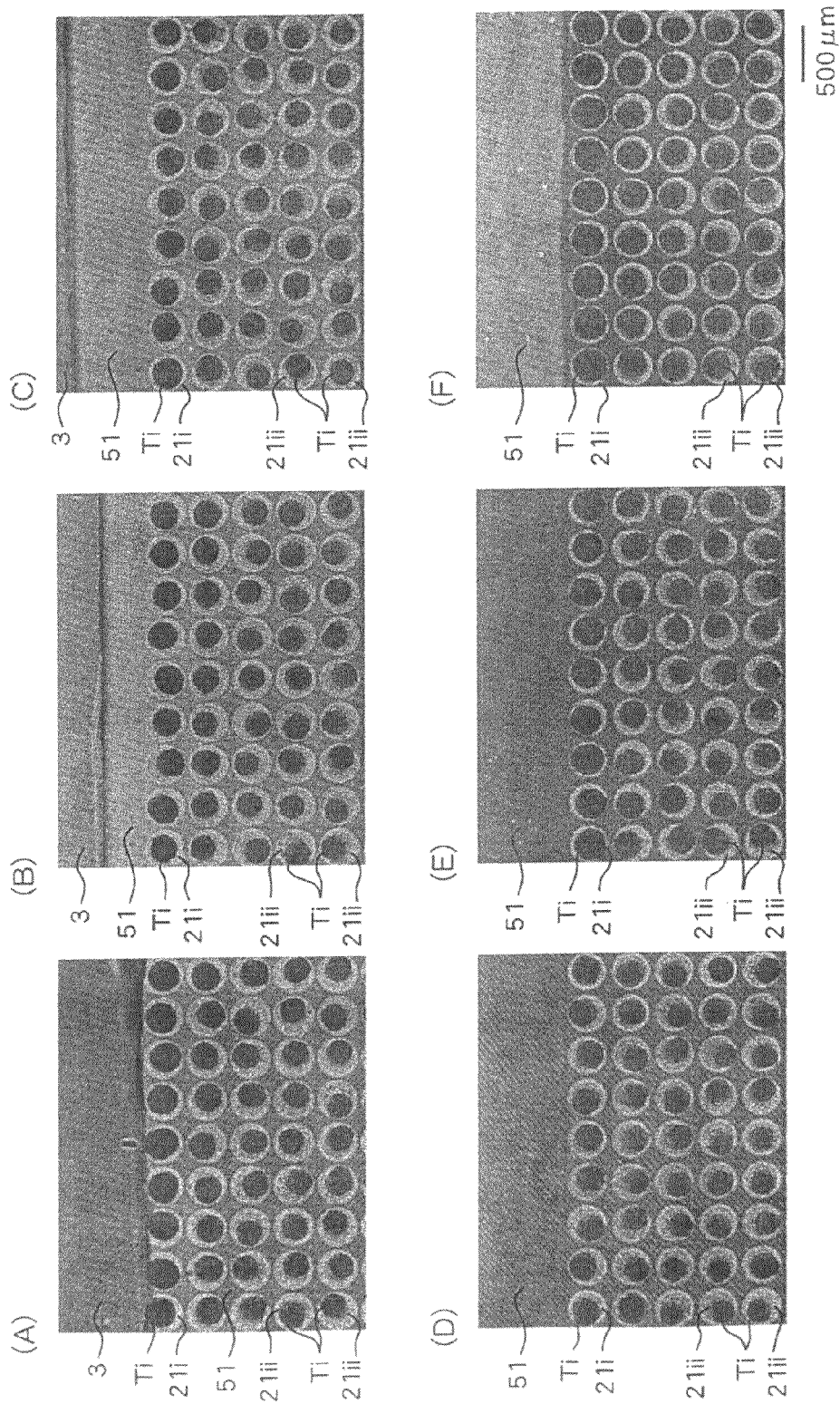

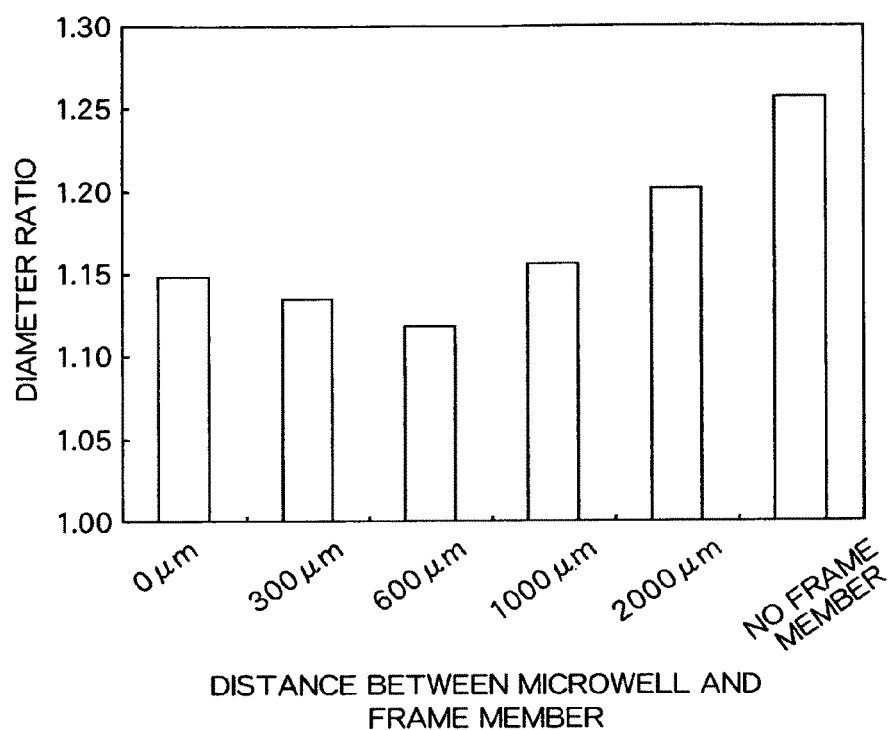

CELL CULTURE INSTRUMENT AND CELL CULTURE METHOD USING THE SAME

TECHNICAL FIELD

The present invention relates to a cell culture instrument and a cell culture method using the same, in particular, a cell culture instrument in which a plurality of wells capable of holding cells therein are formed and a cell culture method using the same.

BACKGROUND ART

Conventionally, for example, a 96-well plate with 96 wells of approximately 3 mm in diameter has been present as a general-purpose cell culture instrument in which a large number of wells capable of holding cells therein are formed (see, for example, Non-patent Document 1, Non-patent Document 2, and Non-patent Document 3). In addition, a 384-well plate with 384 smaller wells and a 1536-well plate with 1536 much smaller wells have been present.

Non-patent Document 1: Hiroshi Kurosawa, Journal of Bioscience and Bioengineering, Vol. 103, No. 5, 389-398, 2007

Non-patent Document 2: Celeste H. Campbell et al., The FASEB Journal Vol. 16 1917-1927, 2002

Non-patent. Document 3: Scott W. Allen et al., DRUG METABOLISM AND DISPOSITION Vol. 29, No. 8, 1074-1079, 2001

DISCLOSURE OF THE INVENTION

Problems to be Solved by the Invention

However, any of the above well plates was based on the premise that operation is performed well by well. That is, in the case of a 96-well plate, the seeding of cells, replacement of culture medium, and so on were manually performed well by well by a user using an instrument, such as a pipette. In addition, in the case of a 384-well plate or a 1536-well plate, an operation, such as injection or recovery of solution, had to be performed well by well using a specialized robot.

On the other hand, for example, when a large number of minute wells capable of holding cells are formed in the surface of a substrate to culture cells therein, the substrate may be fully immersed in a culture medium to perform a cell culture operation, such as seedling of cells and replacement of culture medium, on the large number of the wells at a time. However, for example, when culturing is performed under a plurality of conditions, such a case requires the use of a plurality of substrates and also requires the use of a sufficient amount of a culture medium for fully immersing each of the substrates. For this reason, for example, when rare kinds of cells and reagents are used, the number of possible culture conditions is restricted.

The present invention have been made in consideration of the above-mentioned problems, and one of objects of the invention is to provide a cell culture instrument which has excellent operability while including a plurality of wells capable of holding cells and a cell culture method using the same.

Means for Solving the Problems

A cell culture instrument according to an embodiment of the present invention for solving the above-mentioned problems is characterized by including a base portion in which a well group including a plurality of first wells capable of holding cells is formed; and a frame portion vertically arranged around the well group of the base portion to form a second well being capable of holding a solution. According to the present invention, there can be provided a cell culture instrument which has excellent operability while including a plurality of wells capable of holding cells.

Further, an opening portion of the first well may have an area in a range of 100 to $1 \times 10^6$ $\mu m^2$. This allows provision of a cell culture instrument which has excellent operability while including a large number of minute wells.

Further, the base portion may consists of a base member and the frame portion may consists of a frame member, the both members being formed independently from each other, the frame member may be provided with a through-hole that corresponds to the well group. and be constituted so as to be attachable to and detachable from the base member, and in a state that the frame member is being attached to the base member, an inner wall of the through-hole may be vertically arranged around the well group to form the second well. This allows a further improvement in operability of culturing cells.

Further, in this case, a plurality of the well groups may be formed apart from each other on the base member, and at least one through-hole that corresponds to one of the plurality of well groups may be formed in the frame member. Further, a plurality of the through-holes, each of which corresponds to one of the plurality of well groups, may be formed in the frame member, and in a state that the frame member is being attached to the base member, the inner wall of each of the plurality of the through-holes may be vertically arranged around one of the corresponding well groups to form a plurality of second wells. This allows independent operation of all or part of a plurality of the well groups.

Further, a first joint portion and a second joint portion, which can be connected to each other, may be formed at corresponding positions on the base member and the frame member, respectively. Further, in this case, a plurality of the well groups may be formed apart from each other in the base member, and the first joint portion may be formed around each of the plurality of the well groups. This allows the simple attachment of a frame member to a base member with more reliability. Further, all or part of a plurality of well groups can be independently operated. Further, one of the first joint portion and the second joint portion may be formed in a convex shape and the other thereof may be formed in a concave shape so that the first joint portion and the second joint portion can be fit together. This allows the positioning between a base member and a frame member simply with reliability. Further, the cell culture instrument may be further provided with a holding member, which integrally holds the base member and the frame member attached to the base member and includes an abutting portion that fixes a relative position between the base member and the frame member by abutting on at least part of the periphery of each of the base member and the frame member. This allows the positioning between a base member and a frame member simply with reliability.

A frame member for a cell culture instrument according to an embodiment of the present invention for solving the above-mentioned problems is characterized by including being constituted so as to be attachable to and detachable from a base member in which a well group including a plurality of first wells capable of holding cells, in which a through-hole corresponding to the well group is formed, and the frame member is to be attached to the base member so that an inner wall of the through-hole is vertically arranged around the well group to form a second well capable of holding a solution. According to the present invention, there can be provided a frame member for constituting a cell culture instrument which has excellent operability while including a plurality of wells capable of holding cells.

A cell culture method according to an embodiment of the present invention for solving the above-mentioned problems is characterized by using any one of the cell culture instruments described above. According to the present invention, there can be provided a cell culture instrument which has excellent operability while including a plurality of wells capable of holding cells.

Further, the cell culture method described above may include the steps of: inoculating cells into one of the well groups corresponding to the second well by injecting a solution containing the cells in the second well of the cell culture instrument in a state that the frame member is attached to the base member; and culturing the cells in the well group in a state that the frame member is removed from the base member. This allows the inoculation of the cells in the well group efficiently with reliability.

The cell culture method described above may include the steps of: culturing cells in the well group; and bringing the cells in one well group corresponding to the second well into contact with a predetermined solution by injecting the predetermined solution into the second well of the cell culture instrument in a state that the frame member is being attached to the base member. This allows the treatment of the cells in the well group efficiently with reliability.

Further, the above-mentioned cell culture method may include the steps of: culturing cells in the plurality of the well groups; and bringing the cells in the plurality of the well groups corresponding to the plurality of the second wells into contact with solutions different from one another by injecting the solutions different from one another into the plurality of the second wells of the cell culture instrument in a state that the frame member is being attached to the base member. This allows the treatment of the cells cultured in the respective well groups with the solutions which are different from one another efficiently with reliability.

BRIEF DESCRIPTION OF THE DRAWINGS

FIG. 2 is a cross-sectional view of an instrument 1 in a separated state taken along a plane corresponding to the line II-II illustrated in FIG. 1.

FIG. 3 is a perspective diagram illustrating an attached state of the example of the cell culture instrument according to the embodiment of the present invention.

FIG. 7 is a cross-sectional view of the instrument 1 in a separated state taken along a plane corresponding to the line VII-VII illustrated in FIG. 6.

FIG. 36 are microphotographs showing still another example of the cell organoids formed in the cell culture instrument according to the embodiment of the present invention.

FIG. 37 is an explanatory view illustrating an example of evaluation results for the diameter of the cell organoids formed in the cell culture instrument according to the embodiment of the present invention.

DETAILED DESCRIPTION OF THE INVENTION

Hereinafter, a cell culture instrument and a culture method using the same according to an embodiment of the present invention is described with reference to the figures. First, the cell culture instrument according to this embodiment (hereinafter, referred to as "instrument 1") is described.

Figure 1:
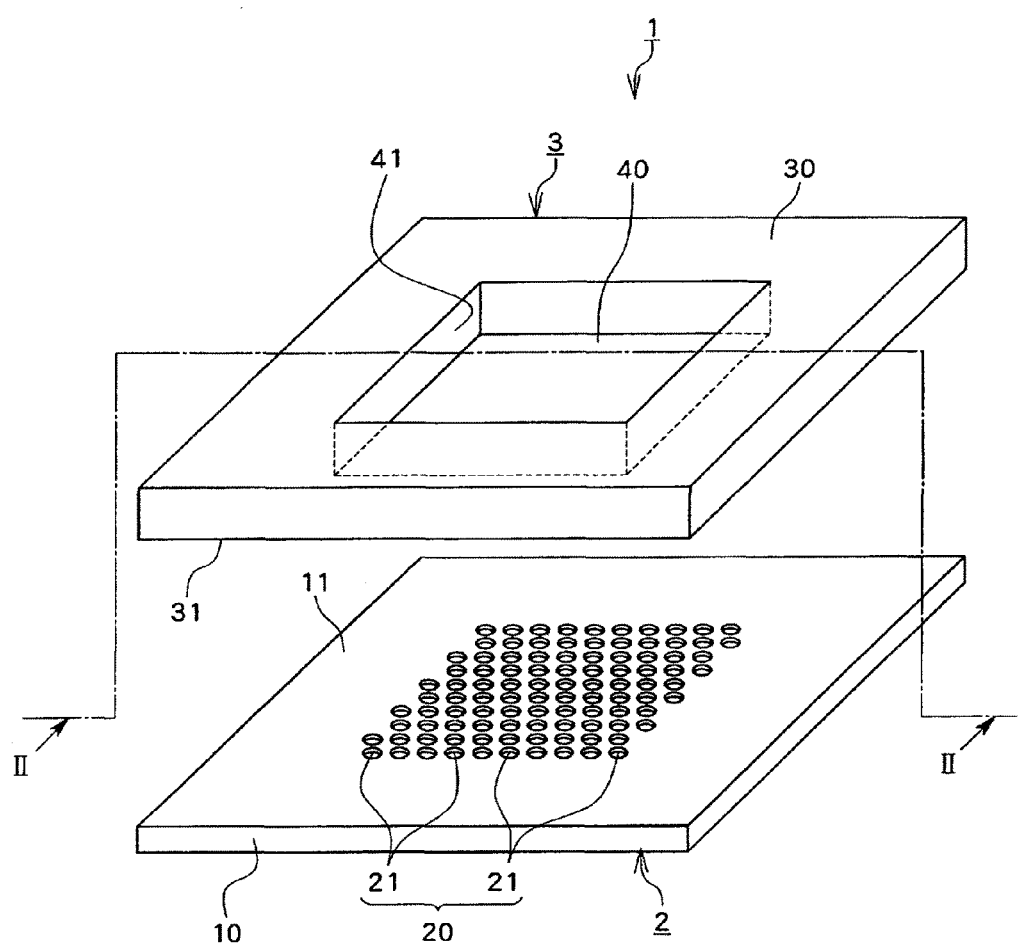
FIG. 1 is a perspective diagram illustrating a separated state of an example of a cell culture instrument according to an embodiment of the present invention.
Figure 4:
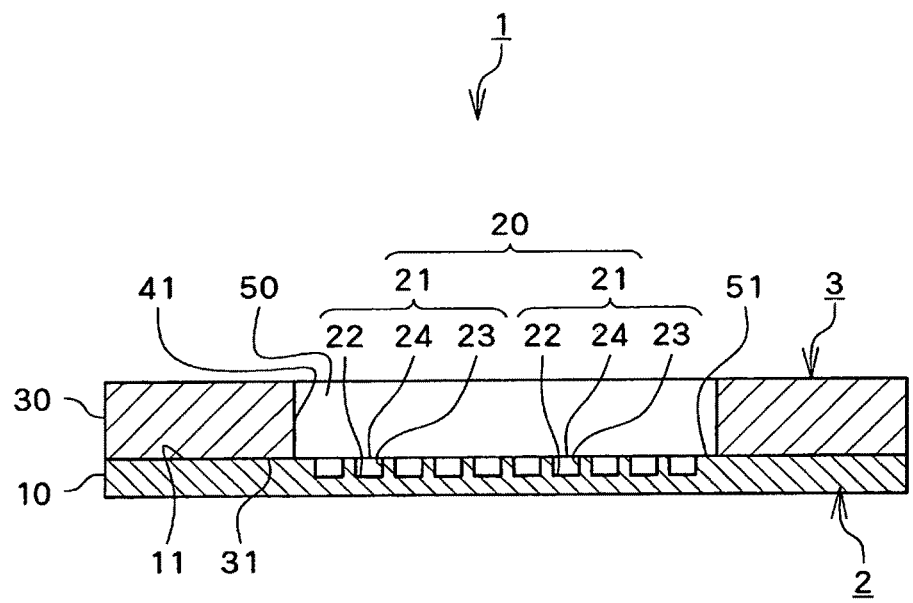
FIG. 4 is a cross-sectional view of the instrument 1 in an attached state taken along the line IV-IV illustrated in FIG. 3.

FIGS. 1 to 4 are explanatory diagrams and views illustrating an example of the instrument 1. As illustrated in FIGS. 1 to 4, the instrument 1 includes a base member 2 and a frame member 3, which is formed as a different member from the base member 2 and is attachable to and detachable from the base member 2. FIG. 1 is a perspective diagram illustrating the instrument 1 in the state where the frame member 3 is being removed from the base member 2 (hereinafter, referred to as a "separated state"). FIG. 2 is a cross-sectional view of the instrument 1 in a separated state taken along a plane corresponding to the line II-II illustrated in FIG. 1. FIG. 3 is a perspective diagram illustrating the instrument 1 in the state where the frame member 3 is being attached to the base member 2 (hereinafter, referred to as an "attached state"). FIG. 4 a cross-sectional view of the instrument 1 in an attached state taken along a plane corresponding to the line IV-IV illustrated in FIG. 3.

As illustrated in FIGS. 1 to 4, one well group (hereinafter, referred to as a "microwell group 20") is formed in the base member 2. In other words, according to this embodiment, the base member 2 includes a first substrate portion 10 formed in the shape of a flat plate with a predetermined thickness. The microwell group 20 is formed in part of the flat surface (hereinafter, referred to as an "upper surface 11") of the upper side of the first substrate portion 10.

The microwell group 20 is constituted by including a plurality of first wells (hereinafter, referred to as "microwells 21") capable of holding cells. Each of the microwells 21 is formed as a bottomed hole opened in the upper surface 11 of the base member 2. In other words, each microwell 21 includes a flat circular bottom 22 and an inner wall 23 provided as a cylindrical inner wall with a predetermined height and vertically arranged around the bottom 22. The plurality of the microwells 21 are regularly arranged at a predetermined interval in a predetermined range of on the upper surface 11 of the first substrate portion 10.

The base member 2 may be formed of an arbitrary material selected depending on the purpose. That is, as the material forming the base member 2, one material may be used alone, or a plurality of materials may be used in combination, each selected from the group consisting of, for example: synthetic resins such as polystyrene, polyethylene, polypropylene, polycarbonate, polyamide, polyacetal, polyester (such as polyethylene terephthalate), polyurethane, polysulfone, polyacrylate, polymethacrylate (such as polymethylmethacrylate (PMMA), and polyvinyl; silicon-based resins such as poly-dimethylsiloxane (PDMS); synthetic rubber such as ethylene propylene diene monomer (EPDM); natural rubber; glass; ceramic; and metal materials such as stainless steel.

In addition, the material forming the base member 2, in particular, the material forming the portion where the microwell group 20 is formed may be preferably a transmissive material, of the materials described above, from a standpoint of, for example, the convenience for observing cells cultured in the microwell group 20 by optical means such as a microscope. In other words, in this embodiment, the first substrate portion 10 may be formed of a transmissive synthetic resin or glass, for example.

Specifically, for example, the first substrate portion 10 is formed of a transmissive synthetic resin, and on part of the upper surface 11 of the first substrate portion 10, a plurality of bottomed holes with a predetermined depth smaller than the thickness of the first substrate portion 10 can be formed as a plurality of microwells 21. In addition, for example, a plurality of through-holes are formed on part of the first flat plate formed of a transmissive synthetic resin, and on one of the surfaces of the first flat plate, where the through-holes are opened, a second flat plate formed of a glass is attached, with the result that the first substrate portion 10 constructed of the first flat plate and the second flat plate can be formed. In this case, the inner surface of each of the through-holes in the first flat plate serves as the inner surface 23 of each microwell 21, and part of the surface of the second flat plate that closes each through-hole serves as the bottom 22 of each microwell 21. In this case, further, both the first flat plate and the second flat plate can be made of the same material.

Any processing method selected depending on the purpose can be used for the formation of the microwells 21. In other words, for example, punching processing using machining center or the like, optical micro-processing using laser or the like, etching processing, emboss processing, or the like, can be used for forming the microwells 21 in part of a previously formed first substrate portion 10. In addition, for example, simultaneously with the formation of the first substrate portion 10, the microwells 21 can be formed in part of the first substrate portion 10 by injection molding, press molding, stereo-lithography, or the like.

The microwells 21 may be formed in arbitrary size depending on the purpose. The microwells 21 are formed in comparatively small sizes within a predetermined range, with the result that for example, a large number of minute microwells 21 can be formed in the base member 2 of several centimeters per side. In this case, a restricted number of scarce cells can be cultured in a large number of the microwells 21. Further, it becomes possible to form a cell organoid of an appropriate size (mass of cells formed as a result of three-dimensional accumulation and bonding of cells) in each microwell 21.

Namely, in each microwell 21, the area of the part opened (hereinafter, referred to as an "opening portion 24") in the surface of the base member 2 (in this embodiment, the upper surface 11 of the first substrate portion 10) can be set, for example, to the range of 100 to $1 \times 10^6$ µm$^2$, and preferably to the range of $7 \times 10^3$ to $5 \times 10^5$ µm$^2$. Specifically, for example, as illustrated in FIGS. 1 to 4, if the opening portion 24 of the microwell 21 is circular, then the diameter of the opening portion 24 may be set to the range of 10 to 1000 µm, and preferably to the range of 100 to 800 µm.

In addition, the area of the bottom 22 of each microwell 21 may be set, for example, to the range of 100 to $1 \times 10^6$ µm$^2$, preferably to the range of $7 \times 10^3$ to $5 \times 10^5$ µm$^2$. Specifically, for example, as illustrated in FIGS. 1 to 4, if the bottom 22 of the microwell 21 is circular, the diameter of the bottom 22 may be set to the range of 10 to 1000 µm, and preferably to the range of 100 to 800 µm.

When the area of the opening portion 24 or bottom 22 is in the above range, many microwells 21 can be formed in a single base member 2. Thus, even scarce cells can be cultured in each of the many microwells 21 which are separated from one another. In this case, cell organoids (for example, spherical spheroids) with uniform size in a predetermined range can be independently formed in each of the many microwells 21. In other words, if the cell organoid becomes larger than a predetermined size, the cells in the cell organoid may not be supplied with sufficient amounts of oxygen and nutrients from the surrounding culture medium. In this regard, when the areas of the opening portion 24 and the bottom 22 of each microwell are equal to or small than the upper limit of the above-mentioned range, there can be reliably formed a large number of cell organoids with appropriate sizes, which are able to maintain their inner cells in a good state. In contrast, when the areas of the opening portion 24 and the bottom 22 of each microwell is larger than the upper limit of the above-mentioned range, cell organoids formed in the respective microwells 21 may become too large in size. In this case, further, a plurality of cell organoids may be formed in one microwell 21. On the other hand, if the area of the opening portion 24 or the bottom 22 is smaller than the lower limit of the above range, it is not easy to reliably hold the cells in each microwell 21. In this case, further, the proliferating cells may plug the microwells 21. In addition, the cells may proliferate so as to make a connection between adjacent microwells 21.

The depth of each microwell 21 (in this embodiment, the height of the inner wall 23 illustrated in FIGS. 2 and 4) is preferably, for example, in the range of 2.5 to 2000 µm. When the depth of the microwell 21 is larger than the upper limit of the above-mentioned range, the cells and the cell organoid held on the bottom 22 of the microwell 21 may not be supplied with sufficient amounts of oxygen and nutrients from the culture medium outside the microwell 21. In contrast, when the depth of the microwell 21 is smaller than the lower limit of the above-mentioned range, the cells or the cell organoid held in the microwell 21 may get out of the microwell 21 during the manipulation of the culture.

In addition, the ratio of the depth of the microwell 21 to the representative length of the opening portion 24 or the bottom 22 of each microwell 21 (the diameter of a circle or the length of the diagonal line of a polygon when the opening portion 24 and the bottom 22 are formed in a circular or polygonal shape) (hereinafter, referred to as an "aspect ratio") is preferably in the range of 0.5 to 2.0. Specifically, for example, if each of the opening portion 24 and the bottom 22 is of a circular shape with a diameter of 5 µm, the depth of the microwell 21 is preferably in the range of 2.5 µm to 10 µm. In addition, for example, if each of the opening portion 24 and the bottom 22 is of a circular shape with a diameter of 1000 µm, the depth of the microwell 21 is preferably in the range of 500 µm to 2000 µm. If the aspect ratio is larger than the upper limit of the above-mentioned range, the cells held on the bottom 22 of each microwell 21 and the cell organoid formed thereon may not be supplied with sufficient amounts of oxygen and nutrients from the culture medium outside the microwell 21. On the other hand, if the aspect ratio is smaller than the lower limit of the above-mentioned range, the cells or the cell organoid held in the microwell 21 may get out of the microwell 21 during the manipulation of the culture.

Here, if the area of the opening portion 24 of each microwell 21, the area of the bottom 22 thereof, and the depth thereof are equal to or smaller than the upper limits of their respective ranges, the volume of a solution which can be held in each microwell 21 becomes very small. Thus, for example, when any operation, such as injection or collection of the solution, is carried out on the respective microwells 21 in a state that the entire base member 2 is exposed in a gas phase, the solution may evaporate from each microwell 21 during the operation to cause disadvantages in the composition of the solution and the-cells in the solution. In this case, therefore, it is preferred to carry out the operation in a state that at least the entire surface portion, where the microwell group 20 is formed, of the base member 2 (in this embodiment, the part, where the microwell group 20 is formed) of the upper surface 11 of the first substrate portion 10 is being immersed in the solution.

The whole or part of the bottom 22 of the microwell 21 can be provided with cellular adhesiveness or cellular non-adhesiveness by selection of the materials of the base member 10 or by surface modification on the bottom 22. In addition, for culturing cells on the bottom 22 of the microwell 21, the inner wall 23 is preferably provided with cellular non-adhesiveness. Here, the cellular adhesive surface refers to, for example, a surface to which cells can be attached with a comparatively flat shape given through the deformation from their spherical shape when the cells are precipitated on the surface in a culture solution. In contrast, the cellular non-adhesive surface refers to, for example, a surface to which cells are attached very weakly while their spherical shape is substantially unchanged when the cells are precipitated on the surface in a culture solution. In this case, the cells on the cellular non-adhesive surface are held in suspension in the solution with their spherical shape kept without attaching to the surface at all or easily detached from the surface by the flow of the culture medium or the like.

For example, the surface of the material that forms the first substrate portion 10 may be directly used as the bottom 22 and the inner wall 23 of the microwell 21. Alternatively, the bottom 22 and the inner wall 23 may be formed as a surface prepared by physically or chemically fixing a cellular adhesive substance or a cellular non-adhesive substance on the surface of the material forming the first substrate portion 10.

The cellular adhesive substance may be any of substances which can be specifically bound to any of cell surface molecules, such as proteins, on the cell membranes of the cells to be used (for example, integrin and sugar chain receptors). In other words, it is possible to suitably select and use, depending on the cell type, a synthesized cellular adhesive material having a protein derived from a biological body (e.g., collagen, fibronectin, and laminin), a specific amino acid sequence exhibiting cellular adhesiveness (such as Arg-Gly-Asp (so-called RGD) sequence), and a specific sugar chain sequence (e.g., galactose side chain).

The cellular non-adhesive substance is not limited to a particular one as long as it is a substance that does not bound to the cell surface molecule, such as protein or sugar chain, present on the cell membrane of the cells used. That is, for example, it is possible to suitably select and use, depending on the cell type, a compound such as a protein derived from a living body (such as albumin), polymers exhibiting remarkably high hydrophilicity in a solution (such as polyethylene glycol and derivatives thereof), MPC (2-methacryloyloxyethyl phosphorylcholine), poly-HEMA (polyhydroxyethylmethacrylate), and SPC (segmented polyurethane).

Those cellular adhesive substances or cellular non-adhesive substances can be immobilized on the bottom 22 and the inner wall 23 of the microwell 21, for example, by drying an aqueous solution containing any of them on the bottom 22 and the inner wall 23, by forming a covalent bond by initiating a chemical reaction (e.g., the condensation reaction between carboxyl groups, amino groups, or the like) between the functional group of the substance and the functional group bounded to the bottom 22 and the inner wall 23, or by binding a metal (e.g., platinum or gold) thin film previously formed on the bottom 22 and the inner wall 23 to the thiol group of the substance in the aqueous solution.

When the whole bottom surface 22 of the microwell 21 is made cellular non-adhesive, a cellar organoid not being attached to the bottom 22 can be formed in the microwell 21. In addition, for example, a cellular adhesive first region is formed in the central portion of the bottom 22 of the microwell 21 and the peripheral portion surrounding the first region serves as a cellular non-adhesive second region, thereby forming a cell organoid being attached to the first region of the bottom 22 in the microwell 21. The formation of the cell organoid in the microwell 21 as described above can particularly be reliably attained in a simple manner when the area of the opening portion 24 or the bottom 22 of the microwell 21 is within the range described above. Note that when the cell organoid is formed in each microwell 21 as described above, it is preferred to provide the inner wall 23 with cellular non-adhesiveness. Naturally, the entire bottom 22 of the microwell 21 is provided with cellular adhesiveness, to thereby allow the cells to be cultured while the cells are two-dimensionally attached to the entire bottom 22.

As illustrated in FIGS. 1 to 4, one window portion 40 is formed in the frame member 3 as a through-hole corresponding to one microwell group 20 formed in the base member 2. In other words, in this embodiment, the frame member 3 includes a second substrate portion 30 formed in the form of a flat plate with a certain thickness, and a rectangle hole passing through the second substrate portion 30 is formed as the window portion 40. The window portion 40 is formed so as to have an opening area which is enough for housing the entire microwell group 20 at a position corresponding to the microwell group 20 of the base member 2 in the second substrate portion 30.

In addition, the frame member 3 is constituted to be attachable to and detachable from the base member 2. In other words, the frame member 3 is constituted to be attachable to the base member 2 so that the microwell group 20 of the base member 2 can be arranged in the window portion 40, and also constituted to be detachable from the base member 2 again after the attachment. Further, the frame member 3 is constituted so that it can be attached to and detached from the base member 2 repeatedly a plurality of times.

Then, as illustrated in FIGS. 3 and 4, in the instrument 1 in an attached state in which the frame member 3 is attached to the base member 2, the frame member 3 is vertically arranged around the microwell group 20 of the base member 2. More specifically, in an attached state, the inner wall 41 of the window portion 40 is vertically arranged around one corresponding microwell group 20. As a result, a second well (hereinafter, referred to as a "macrowell 50"), which is capable of holding a solution and corresponds to the window portion 40, is formed in the instrument 1.

That is, the macrowell 50 is formed as a bottomed hole having a bottom 51 in which one microwell group 20 is formed and an inner wall 41 of the window portion 40. The bottom 51 of the macrowell 50 is a surface portion, where one microwell group 20 is formed, of the base member 2 (in this embodiment, the portion, where the microwell group 20 is formed, of the upper surface 11 of the first substrate portion 10). Then, for example, when a solution is injected into the macrowell 50 in a state that the instrument 1 in an attached state is being placed in a gas phase, the macrowell 50 can hold the solution in the inner space surrounded by the bottom 51 and the inner wall 41 without causing leakage of the solution to the outside of the macrowell 50.

The area of the bottom 51 of the macrowell 50 can be set, for example, to the range of 1 to 2500 mm$^2$, preferably to the range of 10 to 1000 mm$^2$. The depth of the macrowell 50 can be set to a depth (i.e., the height of the inner wall 41, surrounding the bottom 51, of the window portion 40) of, for example, 50 μm or more, preferably 500 μm or more, more preferably 1000 μm or more. When the area of the bottom 51 and the height of the macrowell 50 are each within the above-mentioned range, a solution can be stably held in the macrowell 50.

The frame member 3 may be formed of an arbitrary material selected depending on the purpose. That is, as the material forming the frame member 3, one material may be used alone, or a plurality of materials may be used in combination, each selected from the group consisting of, for example: synthetic resins such as polystyrene, polyethylene, polypropylene, polycarbonate, polyamide, polyacetal, polyester (such as polyethylene terephthalate), polyurethane, polysulfone, polyacrylate, polymethacrylate (such as PMMA), and polyvinyl; silicon-based resins such as PDMS; synthetic rubber such as EPDM; natural rubber; glass; ceramic; and metal materials such as stainless steel.

Further, where at least the surface portion, surrounding the window portion 40, of the frame member 3 is formed of a material which can be adhesive to the surface portion of the base member 2 around the macrowell group 20, the frame member 3 can be constituted to be attachable to the base member 2 without the formation of any specific part on the instrument 1 for attaching the frame member 3 to the base member 2. In this case, further, the macrowell 50, which is able to hold a solution while the instrument 1 is in an attached state, can be reliably formed in a simple manner. Such a material with high adhesiveness can be suitably selected in combination with a material forming the base member 2. That is, for example, of the above-mentioned materials used for the formation of the frame member 3, it is preferred to use a silicon-based resin such as PDMS or an elastic resin (elastomer resin) such as synthetic rubber and natural rubber.

Specifically, for example, the first substrate portion 10 is formed of a transmissive synthetic resin and, on the other hand, a silicon-based resin can be used to form the entire second substrate portion 30 or the portion, surrounding the window portion 40, of the flat surface on the lower side of the second substrate portion 30 (hereinafter, referred to as a "lower surface 31"). In this case, for attaching the frame member 3 to the base member 2, the frame member 3 is positioned with the base member 2 and the lower surface 31 of the frame member 3 is press-contacted with the upper surface 11 of the base member 2 so that the microwell group 20 is housed in the window portion 40. Thus, the inner wall 41 of the window portion 40 can be adhered to and vertically arranged on the upper surface 11 around the microwell group 20.

Any processing method selected depending on the purpose can be used for the formation of the window portion 40. In other words, for example, punching processing using machining center or the like, optical micro-processing using laser or the like, etching processing, emboss processing, or the like, can be used for forming the window portion 40 in part of a previously formed second substrate portion 30. In addition, for example, simultaneously with the formation of the second substrate portion 30, the window portion 40 can be formed in part of the second substrate portion 30 by injection molding, press molding, stereo-lithography, or the like.

Figure 5:
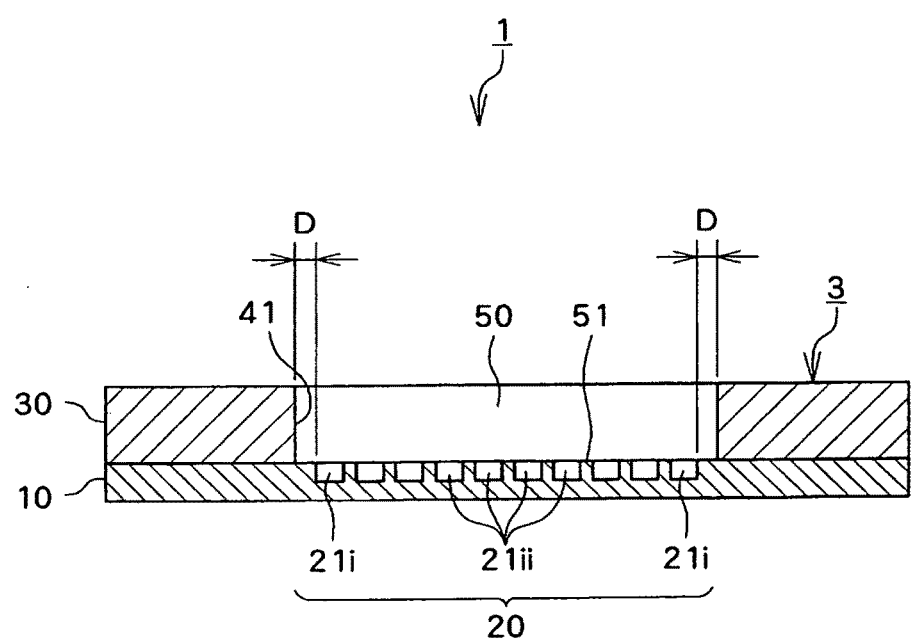
FIG. 5 is a cross-sectional view for illustrating another aspect of the example of the cell culture instrument according to the embodiment of the present invention.

FIG. 5 illustrates a cross-sectional view of the same instrument 1 as one illustrated in FIG. 4 in order to describe the other aspect of the instrument 1. As illustrated in FIG. 5, the microwell group 20 includes microwells formed at the position nearest to the frame member 3 (hereinafter, referred to as "marginal wells 21$i$") and constituting the marginal portion of the microwell group 20 and microwells formed at the position comparatively far from the frame member 3 (hereinafter, referred to as "central wells 21$ii$") and constituting the central portion of the microwell group 20.

As mentioned above, in the microwell group 20, cells which can be bonded to one another may be cultured to allow the formation of one cell organoid as a three-dimensional aggregate of the cells in each of the marginal wells 21$i$ and the central wells 21$ii$.

In this case, in spite of the formation of both the marginal well 21$i$ and central wells 21$ii$ in the same shape and size, the size of the cell organoid formed in the marginal well 21$i$ (hereinafter, referred to as a "marginal organoid") is, in some cases, different in size from the cell organoid formed in the central wells 21$ii$ (hereinafter, referred to as a "central organoid"). In other words, for example, the size of the marginal organoid tends to be larger than that of the central organoid.

In this respect, the inventors of the present invention have intensively studied and uniquely found that the size of the marginal organoid can be made as close as possible to the size of the central organoid by setting the distance D between the marginal well 21$i$ and the frame member 3 (in the example illustrated in FIG. 5, the distance D between the end of the marginal well 21$i$ on the side of the frame member 3 and the inner wall 41 of the frame member 3) to a value equal to or less than a minute predetermined threshold value.

In other words, the distance D is preferably 5.0 mm or less, more preferably 2.0 mm or less, and particularly preferably 1.0 mm or less. By setting the distance D within the above-mentioned range, the ratio of the size of the marginal organoid to that of the central organoid may be set to, for example, 1.25 or less, or further, 1.20 or less.

The more the distance D decreases, the nearer the marginal well 21$i$ approaches to the frame member 3, leading to an increase in difficulty of operating or observing the cell culture in the marginal well 21$i$. In this case, however, the frame member 3 is attachable to and detachable from the base member 2. Thus, for example, the frame member 3 may be detached from the base member 2 as required to operate or observe the cell culture while those members are being separated.

Therefore, by reducing the above distance D within the above minute range in the instrument 1 while using the instrument 1 having the base member 2 and the frame member 3 which are attachable to and detachable from each other, it becomes possible to form and culture one cell organoid with extremely uniform size in each of the marginal wells 21$i$ and central wells 21$ii$.

Figure 6:
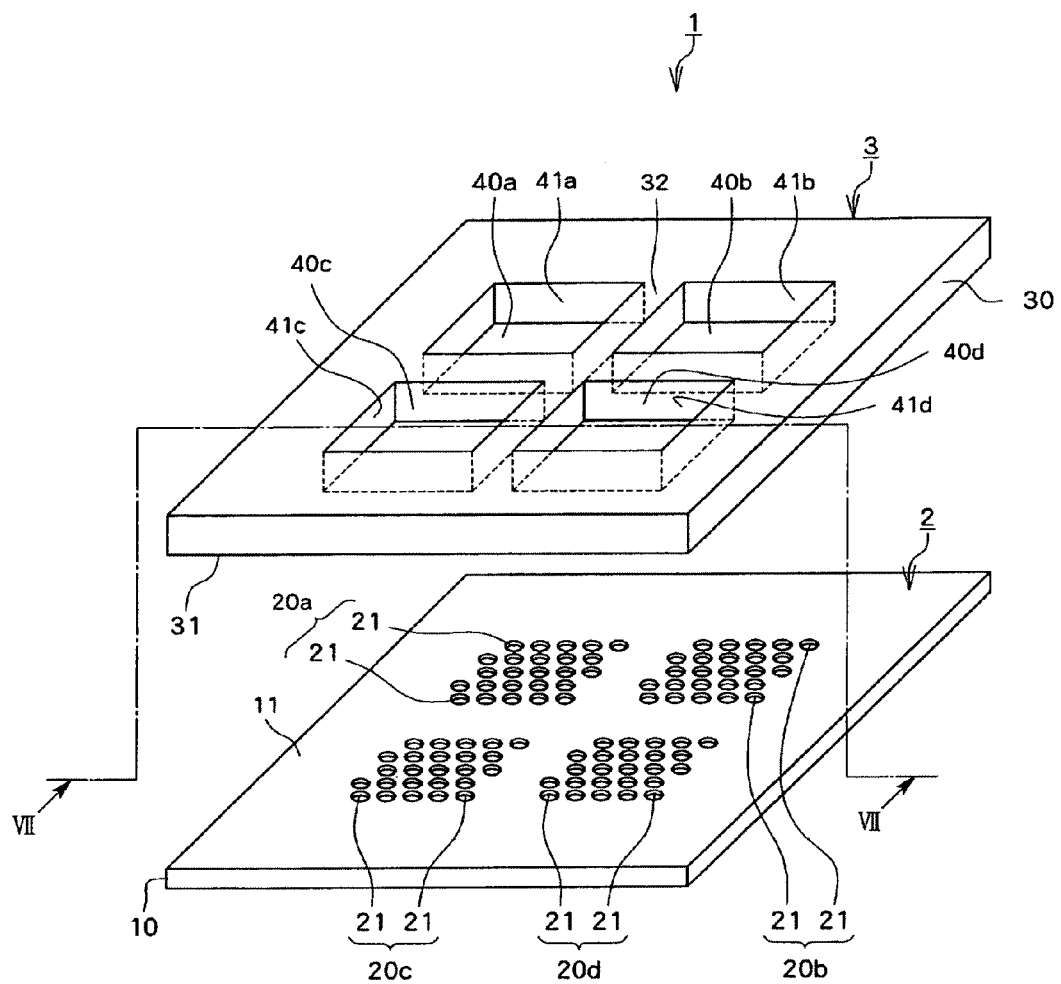
FIG. 6 is a perspective diagram illustrating a separated state of another example of the cell culture instrument according to the embodiment of the present invention.
Figure 8:
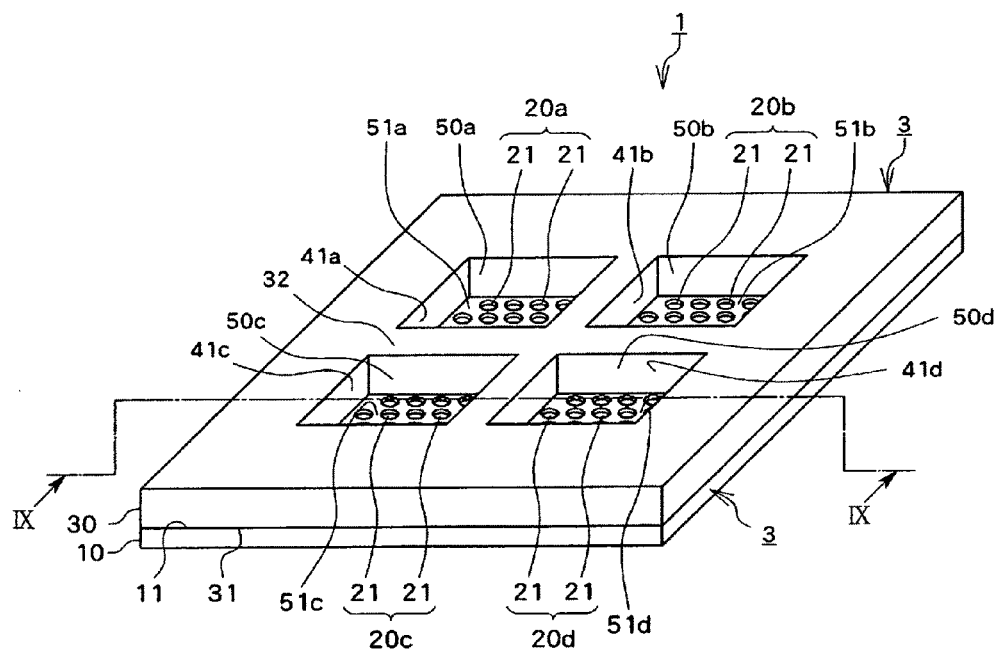
FIG. 8 is a perspective diagram illustrating an attached state of the another example of the cell culture instrument according to the embodiment of the present invention.
Figure 9:
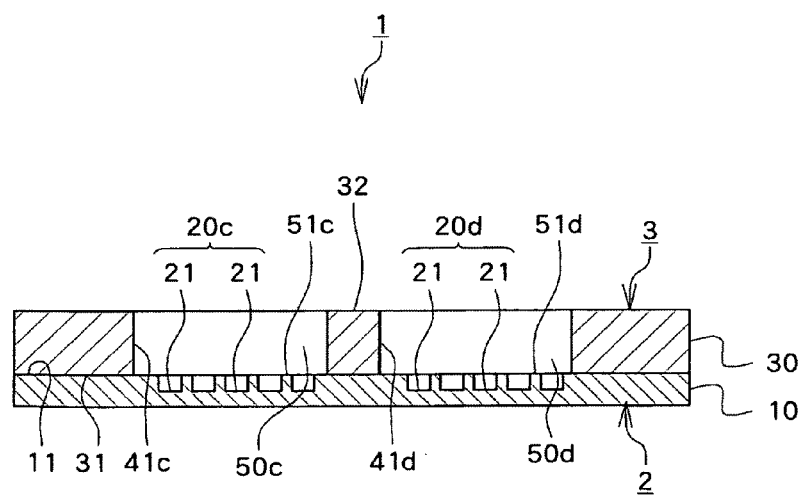
FIG. 9 is a cross-sectional view of the instrument 1 in an attached state taken along the line IX-IX illustrated in FIG. 8.

In addition, a plurality of microwell groups 20 maybe formed at a predetermined distance from one another in the base member 2. In this case, at least one window portion 40 each corresponding to one of the plurality of the microwell groups 20 can be formed in the frame member 3. FIGS. 6 to 9 are explanatory diagrams and views illustrating an example of the instrument 1 in this case. FIG. 6 is a perspective diagram of the instrument 1 in a separated state. FIG. 7 is a cross-sectional view of the instrument 1 in a separated state taken along a plane corresponding to the line VII-VII illustrated in FIG. 6. FIG. 8 is a perspective diagram of the instrument 1 in an attached state. FIG. 9 is a cross-sectional view of the instrument 1 in an attached state taken along a plane corresponding to the line IX-IX illustrated in FIG. 8. Note that, for the instrument 1 according to the following example, the same portions as those in the above examples illustrated in FIGS. 1 to 4 are given the same reference numerals and the detail descriptions of their duplication is omitted.

As illustrated in FIGS. 6 to 9, four microwell groups 20$a$ to 20$d$ are formed at a predetermined distance from one another in the base member 2. The microwell groups 20$a$ to 20$d$ include a plurality of microwells 21 which are capable of holding cells.

On the other hand, four window portions 40$a$ to 40$d$ each corresponding to one of the four microwells 20$a$ to 20$d$ of the base member 2 are formed in the frame member 3. In other words, four window portions 40$a$ to 40$d$ are formed at respective positions each independently corresponding to one of the four microwell groups 20$a$ to 20$d$. As a result, the frame member 3 includes a partition portion 32 formed in cross shape to partition four window portions 40$a$ to 40$d$ from one another.

Further, as illustrated in FIGS. 8 and 9, in the instrument 1 in an attached state, the inner walls 41$a$ to 41$d$ of the respective window portions 40$a$ to 40$d$ (see FIGS. 6 and 7) are vertically arranged around one of the four microwell groups 20$a$ to 20$d$ corresponding to the respective window portions 40$a$ to 40$d$. As a result, four macrowells 50$a$ to 50$d$, which are partitioned by the partition portion 32 of the frame member 3, are formed in the instrument 1. Each of the four microwell groups 20$a$ to 20$d$ corresponding to the bottoms 51$a$ to 51$d$ is formed in each of the bottoms 51$a$ to 51$d$ of the respective macrowells 50$a$ to 50$d$.

Further, the peripheral portion of each of at least four window portions 40$a$ to 40$d$ of the lower surface 31 of the frame member 3 is firmly attached to the peripheral portion of each of at least four microwell groups 20 of the upper surface 11 of the base member 2. As a result, four macrowells 50$a$ to 50$d$ are formed so that they can hold solutions independently from one another.

Figure 10:
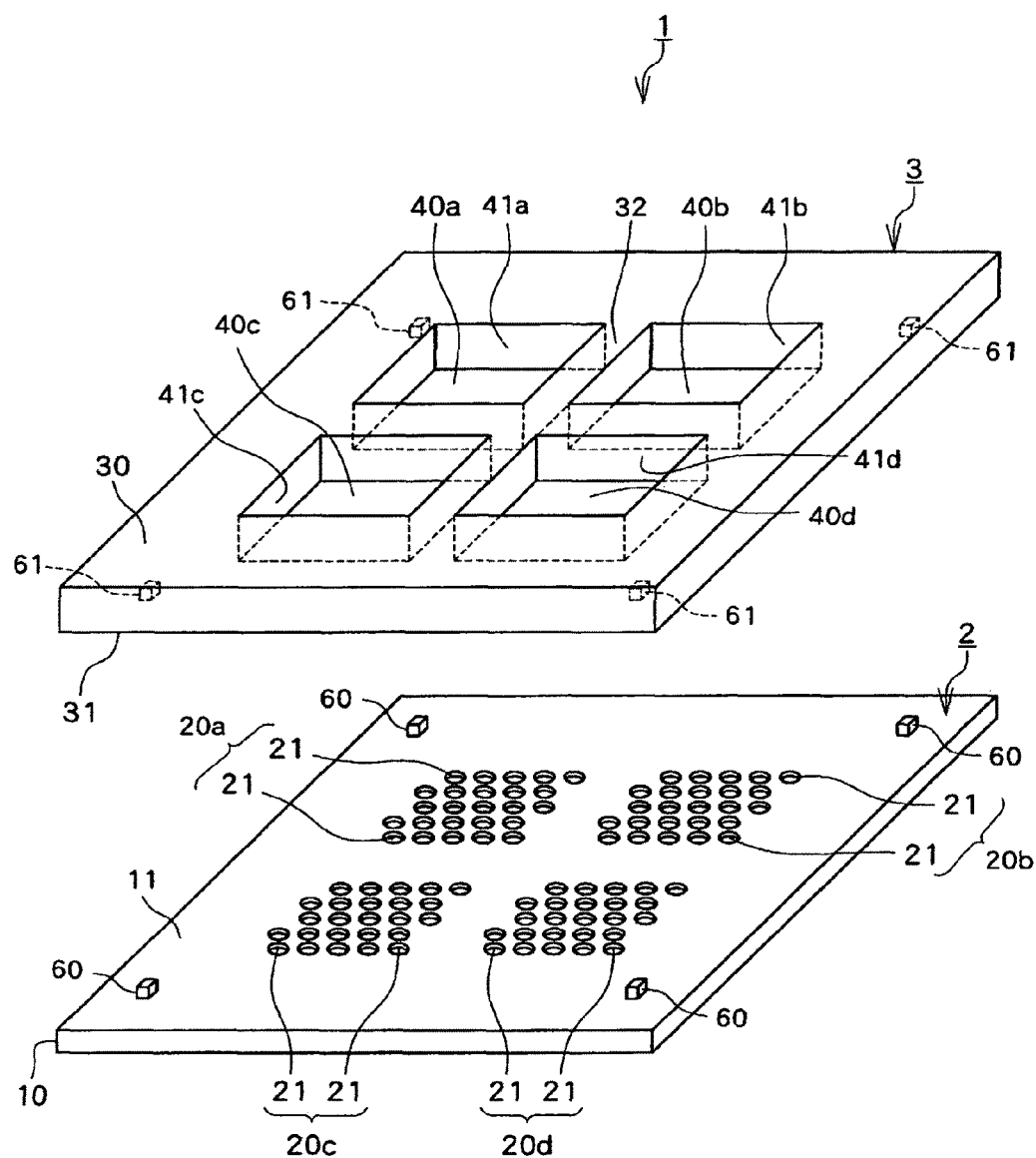
FIG. 10 is a perspective diagram illustrating a separated state of an example of a cell culture instrument having a joint portion according to the embodiment of the present invention.

In addition, in both the base member 2 and the frame member 3, a first joint portion and a second joint portion which can be connected to each other are formed on the corresponding positions. FIG. 10 is a perspective diagram of the separated state of the instrument 1 according to the example illustrated in FIGS. 6 to 9 as an example of the case where the first joint portion and the second joint portion are formed.

In the instrument 1 illustrated in FIG. 10, four convexed first joint portions (hereinafter, referred to as "fitting protrusions 60") protruded at a predetermined height from the upper surface 11 are formed on the part of the periphery of the upper surface 11 of the first substrate portion 10, where the periphery surrounds all of four microwell groups 20$a$ to 20$d$. On the other hand, four concaved, bottomed holes of a predetermined depth (hereinafter, referred to as "fitting holes 61") are formed in the part of the periphery of the lower surface 31 of the second substrate portion 30, where the periphery surrounds all of four window portions 40a to 40d, at positions corresponding to the respective four fitting protrusions 60 of the first substrate portion 10.

Those fitting protrusions 60 and the fitting holes 61 are formed in the corresponding shapes so that they can be fit to each other. By fitting the fitting protrusions 60 of the base member 2 to the corresponding fitting holes 61 of the frame member 3, the frame member 3 is attached to the base member 2 to form the instrument 1 in an attached state as illustrated in FIGS. 8 and 9. In this case, the base member 2 and the frame member 3 can be simply and reliably combined together with the predetermined positional relationship.

Figure 11:
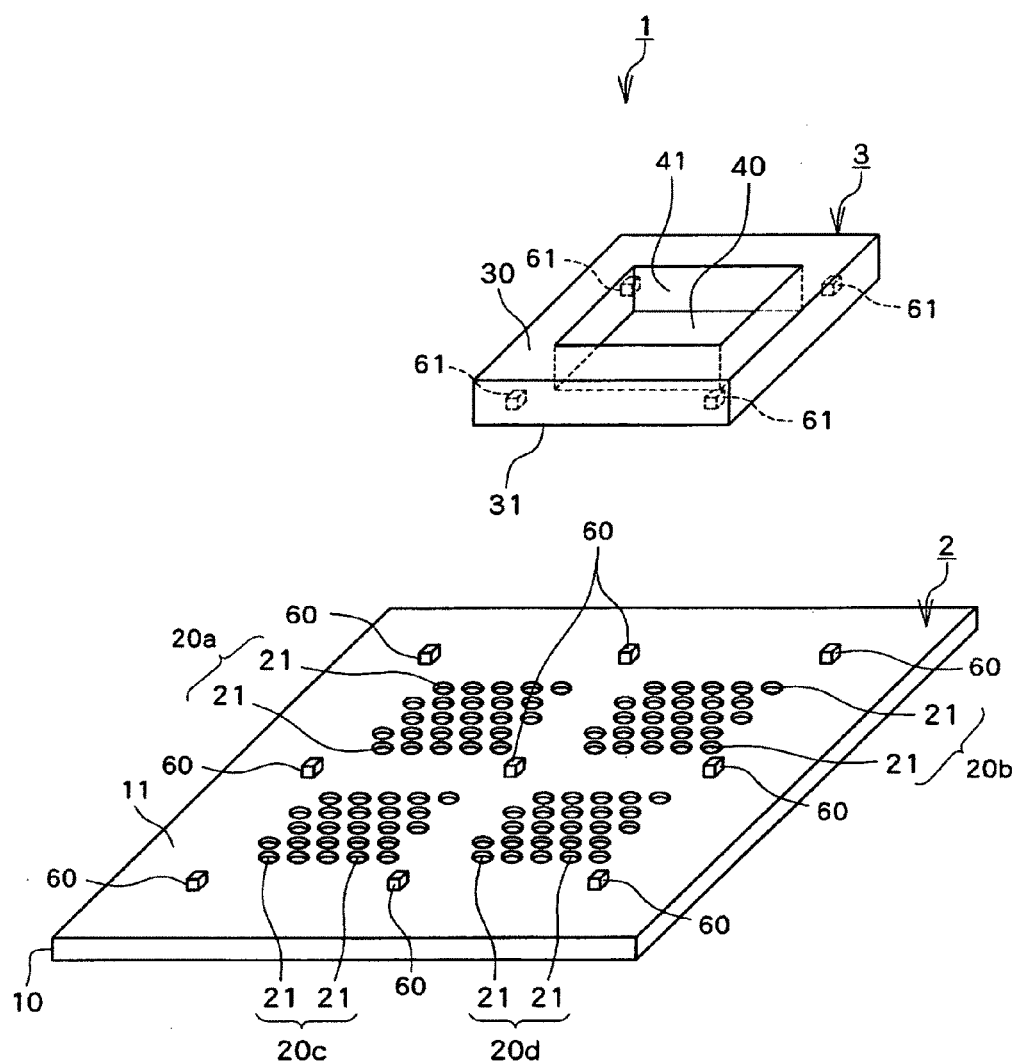
FIG. 11 is a perspective diagram illustrating a separated state of another example of the cell culture instrument having a joint portion according to the embodiment of the present invention.
Figure 12:
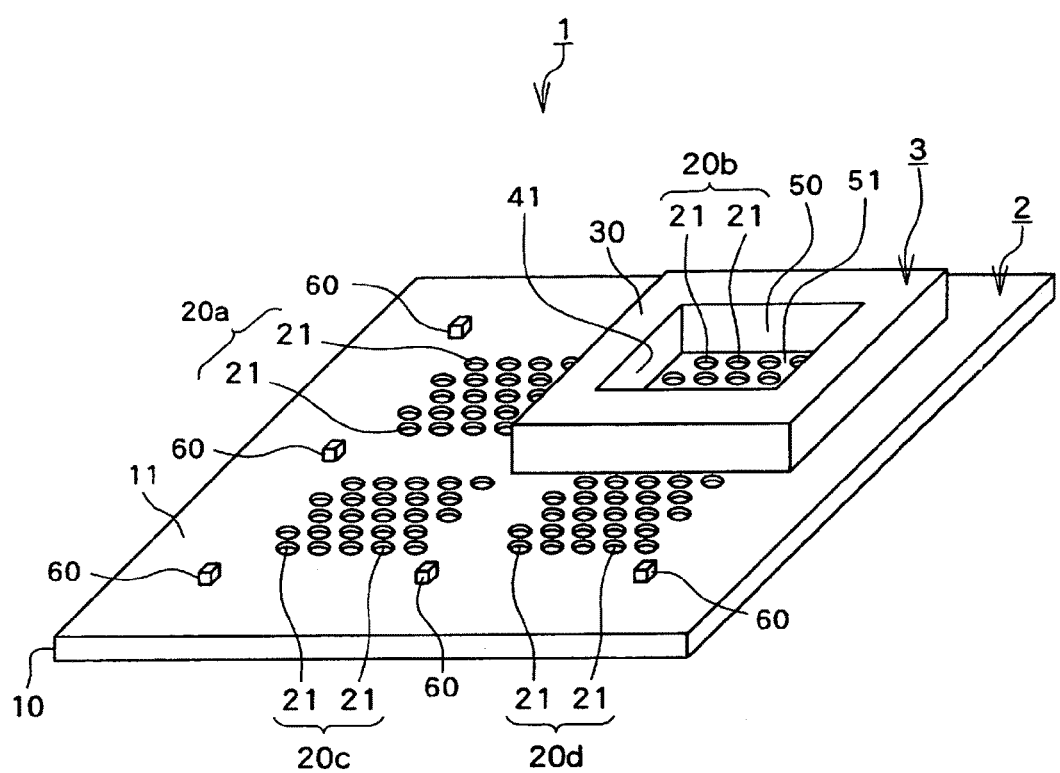
FIG. 12 is a perspective diagram illustrating an attached state of the another example of the cell culture instrument having a joint portion according to the embodiment of the present invention.

In addition, when a plurality of microwell groups 20 are formed apart from each other in the base member 2, joint portions which are connectable to part of the frame member 3 may be formed around each of the plurality of the microwells 20 of the base member 2. FIGS. 11 and 12 are perspective diagrams of an example of the instrument 1 in this case, which represent a separated state and an attached state thereof, respectively.

The instrument 1 illustrated in FIGS. 11 and 12 is provided with four fitting protrusions 60 on the periphery of each of four microwell groups 20a to 20d on the upper surface 11 of the first substrate portion 10. On the other hand, only one window portion 40 corresponding to one of four microwells 20a to 20d of the base member 2 is formed in the frame member 3. In addition, four fitting holes 61 are formed around the window portion 40 of the lower surface 31 of the frame member 3 at positions corresponding to four fitting protrusions 60 formed around the respective microwell groups 20a to 20d of the base member 2, where the four fitting holes 61 are shaped for fitting to four fitting protrusions 60.

Then, as illustrated in FIG. 12, the inner wall 41 of one window portion 40 is vertically arranged only around a microwell group 20b among four microwell groups 20a to 20d in the instrument 1 in an attached state. As a result, one macrowell 50 is formed in the base member 2. One microwell group 20b is formed in the bottom 51 of the macrowell 50.

Further, since four fitting protrusions 60 are formed in the same arrangement on the periphery of each of four microwell groups 20a to 20d, the frame member 3 is configured to correspond to any of the four microwell groups 20a to 20d. In other words, the frame member 3 may be attached to the periphery of any one of four microwell groups 20a to 20d to form one macrowell 50 with the bottom 51 where any one of the four microwell groups 20a to 20d is formed.

In addition, for example, in the frame member 3 in which four window portions 40 are formed as illustrated in FIG. 10 described above, four fitting holes 61 corresponding to the fitting protrusions 60 illustrated in FIGS. 11 and 12 may be formed around their respective four window portions 40. In addition, by respectively fitting the fitting protrusions 60 of the base member 2 to the corresponding fitting holes 61 of the frame member 3, the frame member 3 is attached to the base member 2 to form the instrument 1 in an attached state as illustrated in FIGS. 8 and 9. In this case, the base member 2 and the frame member 3 can be simply combined together with the predetermined positional relationship with more reliability.

Although the example in which one through-hole 40 is formed in the frame member 3 is represented in FIGS. 11 and 12, a plurality of corresponding through-holes 40 may be formed in some of a plurality of microwell groups 20 in the frame member 3. In other words, for example, two through-holes 40 may be formed in the frame member 3 so that they respectively correspond to two microwell groups 20a and 20b among four microwell groups 20a to 20d as illustrated in FIGS. 11 and 12. In this case, two macrowells 50 can be formed in the instrument 1 in an attached state such that the inner wall 41 of the window portion 40 is vertically arranged around only each of two microwell groups 20a and 20b among four microwell groups 20a to 20d.

Figure 13:
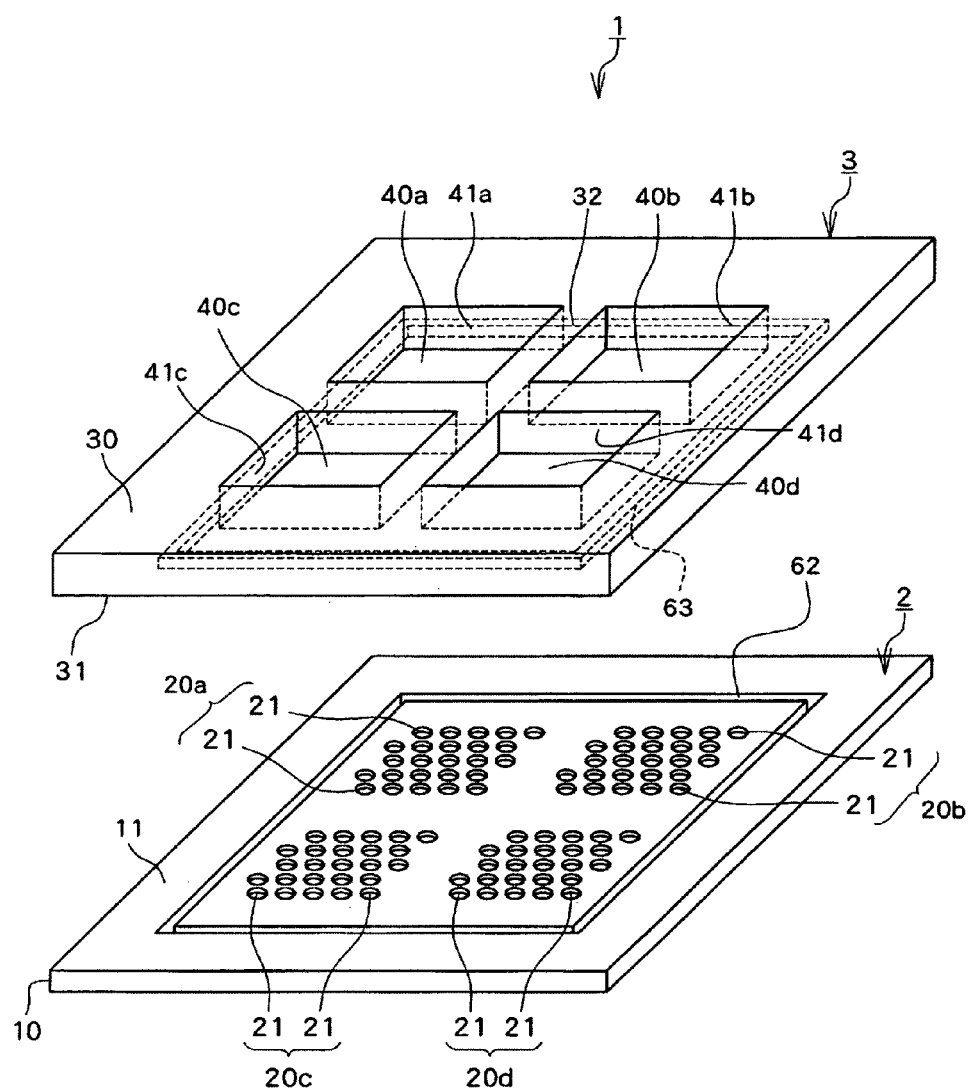
FIG. 13 is a perspective diagram illustrating a separated state of still another example of the cell culture instrument having a joint portion according to the embodiment of the present invention.

FIG. 13 is a perspective diagram of the separated state of the instrument 1 as another example where a first joint portion and a second joint portion are formed. In the instrument 1 illustrated in FIG. 13, a trench-shaped first joint portion (hereinafter, referred to as a "trench portion 62") is formed in the upper surface of the first substrate portion 10, where the trench portion 62 with a predetermined depth surrounds all of four microwell groups 20a to 20d. On the other hand, a bank-shaped second joint portion (hereinafter, referred to as a "bank portion 63") is formed in the lower surface 31 of the second substrate portion 30 so as to correspond to the trench portion 62 of the first substrate portion 10. The bank portion 63 with a predetermined height surrounds all of four window portions 40a to 40d. The trench portion 62 and the bank portion 63 are formed in the corresponding shapes so that they can fit to each other.

In addition, by respectively fitting the trench portion 62 of the base member 2 to the bank portion 63 of the frame member 3, the frame member 3 is attached to the base member 2 to form the instrument 1 in an attached state as illustrated in FIGS. 8 and 9. In this case, the base member 2 and the frame member 3 can be simply combined together with the predetermined positional relationship with reliability.

Figure 14:
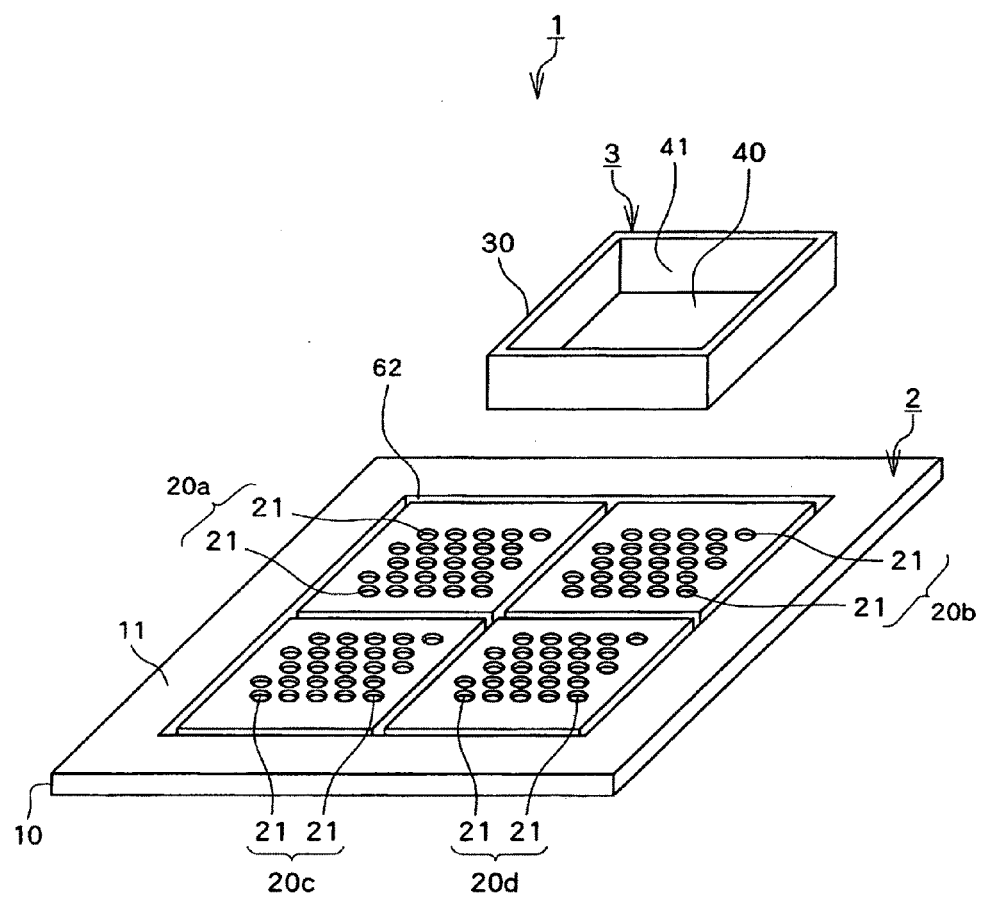
FIG. 14 is a perspective diagram illustrating a separated state of the still another example of the cell culture instrument having a joint portion according to the embodiment of the present invention.

In addition, when a plurality of microwell groups 20 are formed apart from each other in the base member 2, joint portions which are connectable to he part of the frame member 3 may be formed around each of the plurality of the microwells 20 of the base member 2. FIG. 14 is a perspective diagram of an example of the instrument 1 in this case, which represents a separated state.

The instrument 1 illustrated in FIG. 14 is provided with the trench portion 62 surrounding the periphery of each of four microwell groups 20a to 20d on the upper surface 11 of the first substrate portion 10. On the other hand, one window portion 40 corresponding to one of four microwells 20a to 20d of the base member 2 is formed in the frame member 3. In addition, the frame member 3 is formed in such as shape so as to fix to part of the trench portion 62 formed around one of the four microwell groups 20a to 20d of the base member 2. Then, as the example illustrated in FIG. 12, the inner wall 41 of one window portion 40 of the frame member 3 is vertically arranged only around one microwell group among four microwell groups 20a to 20d in the instrument 1 in an attached state. As a result, one macrowell 50 is formed.

Further, since each of the trench portions 62 is formed in the same arrangement on the periphery of each of four microwell groups 20a to 20d, the frame member 3 is configured to correspond to each of the four microwell groups 20a to 20d. In other words, the frame member 3 may be attached to the periphery of any one of four microwell groups 20a to 20d to form one macrowell 50 with the bottom 51 where any one of the four microwell groups 20a to 20d is formed.

The frame member 3 having four window portions 40 as illustrated in FIG. 13 as described above can also be used when the trench portion 62 such as one illustrated in FIG. 14 is formed in the base member 2. In this case, the bank portion 63 of the frame member 3 (see FIG. 13) may be a lattice-shaped one extending around each of four window portions 40 of the frame member 3 while corresponding to the trench portion 62 of the base member 2 illustrated in FIG. 14. By fitting the bank portion 63 of the frame member 3 to the trench portion 62 of the base member 2, the frame member 3 is attached to the base member 2 to form the instrument 1 in an attached state as illustrated in FIGS. 8 and 9. In this case, the base member 2 and the frame member 3 can be simply combined together with the predetermined positional relationship with more reliability.

Figure 15:
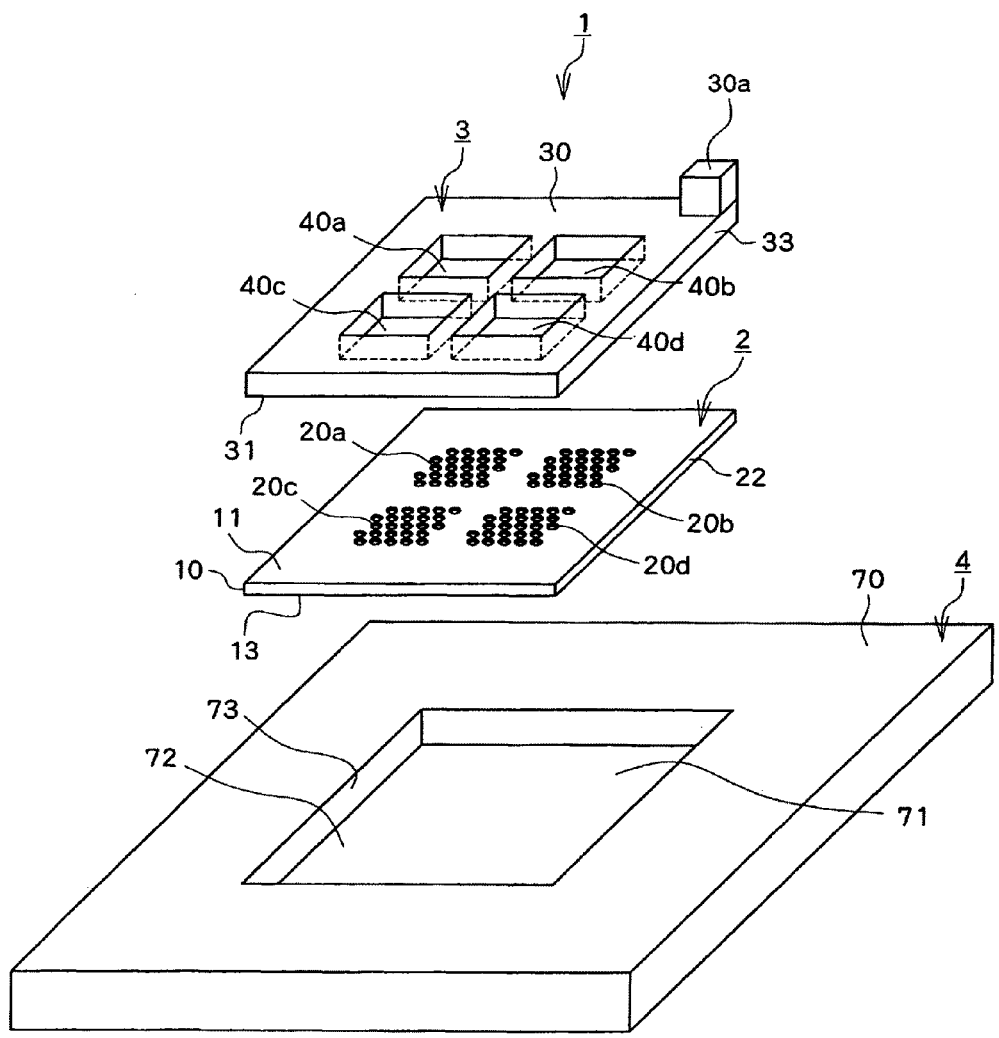
FIG. 15 is a perspective diagram illustrating a separated state of an example of a cell culture instrument having a holding member according to the embodiment of the present invention.
Figure 16:
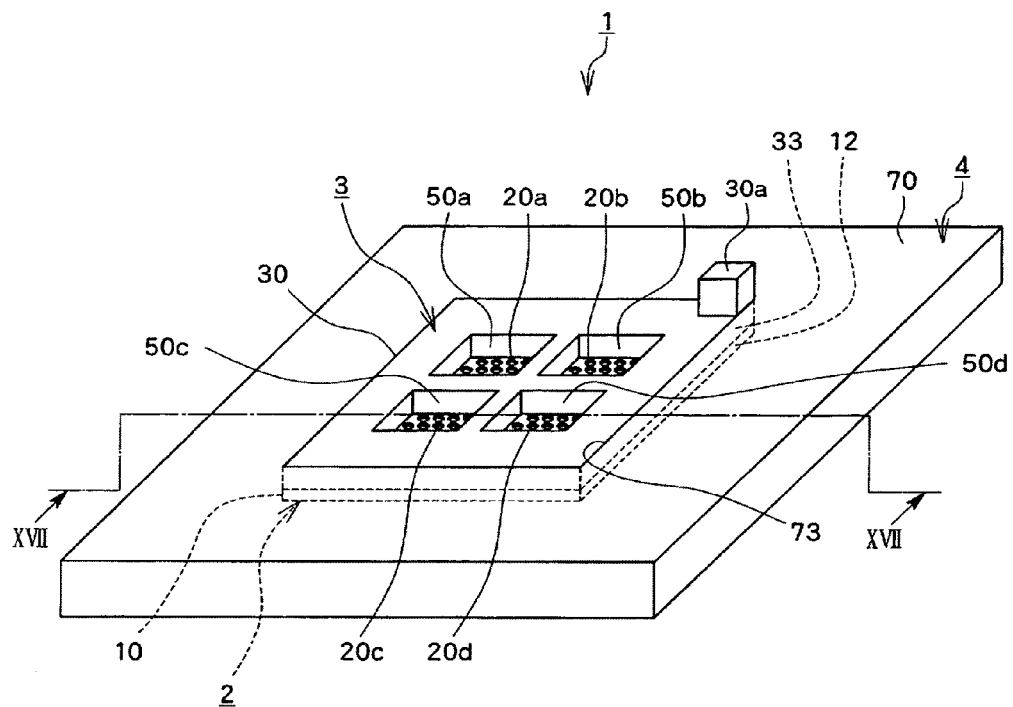
FIG. 16 is a perspective diagram illustrating an attached state of the example of the cell culture instrument having a holding member according to the embodiment of the present invention.
Figure 17:
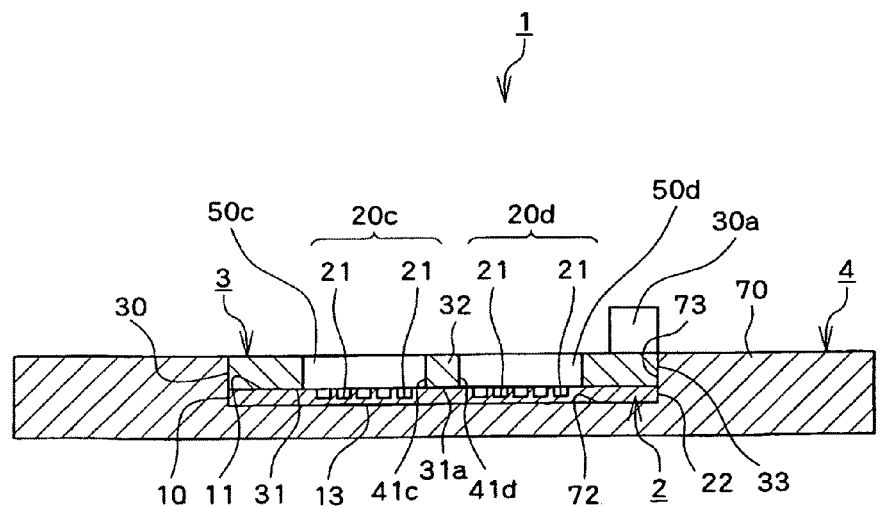
FIG. 17 is a cross-sectional view of the cell culture instrument in an attached state taken along the XVII-XVII line illustrated in FIG. 16.

Further, the instrument 1 may further include a holding member for integrally holding the base member 2 and the frame member 3 attached to the base member 2. In this case, the holding member has an abutting portion that abuts at least part of the periphery of each of the base member 2 and the frame member 3 to fix the relative position between the base member 2 and the frame member 3. FIGS. 15 to 17 are explanatory diagrams and views illustrating an example of the instrument 1 in this case. FIGS. 15 and 16 are perspective diagrams of an example of the instrument 1 in this case, which represent a separated state and an attached state thereof, respectively. FIG. 17 is a cross-sectional view of the instrument 1 in an attached state taken along a plane corresponding to the XVII-XVII illustrated in FIG. 16.

As illustrated in FIGS. 15 to 17, the instrument 1 includes a base member 2, a frame member 3, and a holding member 4. The holding member 4 is provided with a third substrate portion 70 formed in the shape of a flat plate with a predetermined thickness. A rectangular bottomed hole for housing both the base member 2 and the frame member 3 (hereinafter, referred to as a "housing portion 71") is formed in the flat surface on the upper side of the third substrate portion 70. The housing portion 71 includes a rectangular flat bottom 72 and an inner wall 73 of a predetermined height vertically arranged around the bottom 72.

In the instrument 1 in an attached state as illustrated in FIGS. 16 and 17, the base member 2 is mounted on the bottom 72 of the housing portion 71. Further, the frame member 3 is housed in the housing portion 71 while being attached to the base member 2. That is, both the base member 2 and the frame member 3 are fit into the housing portion 71 of the holding member 4 while being stacked. Thus, both, the periphery 22 of the base member 2 and the periphery 33 of the frame member 3 attached to the base member 2 abut the inner wall 73 of the housing portion 71. As a result, in the instrument 1, both the base member 2 and the frame member 3 can be simply and reliably held while being kept in a predetermined positional relationship.

Further, as illustrated in FIGS. 15 to 17, part of the frame member 3 of this example is provided with a convexed handle portion 30a protruded upward. Thus, the operator can easily attach the frame member 3 to the base member 2 or detach the frame member 3 from the base member 2 by pinching the handle portion 30a with a pair of tweezers or the like. The handle portion 30a may be integrally formed at the time of shaping the frame member 3. Alternatively, it may be additionally formed on the previously-formed frame member 3. In this case, the convexed handle portion 30 may be not only limited to be formed on the frame member 3 of the above-mentioned example or another example described below. Alternatively, it may be formed in any shape on any kind of the frame member 3 in accordance with the present invention.

Next, a cell culture method according to this embodiment (hereinafter, referred to as the "present method") is described. In this method, cells are cultured in the microwell group 20 of the instrument 1. Here, any cell may be used depending on the purpose without regard to the animal species, the type of organ or tissue, or the like from which cells are originated.

Specifically, for example, the cells which can be used may be primary cells (stem cells or embryonic stem cells (ES)) originated from any organ or tissue (such as the liver, pancreas, kidney, neuron, or skin) of the human or any of other animals (such as a monkey, pig, dog, rat, or mouse), an established cell line, or cells obtained by subjecting any of them to gene manipulation or the like. In addition, the cells that can be used may be of a single kind of cells alone or may be a combination of a plurality of kinds of cells at any ratio. In addition, for the formation of a cell organoid, the cells that are preferably used are those which can be bonded together.

In addition, the solution used for the cell culture may be any kind of aqueous solution that contains appropriate concentrations of desired salts, nutrients, and so on to maintain the viable state, functions, and so on of the cells used. Specifically, for example, the solution that can be used may be a culture medium, such as one prepared by addition of an antibiotic or the like to a basal medium, such as the Dulbecco's Modified Eagle's Medium (DMEM), or a so-called physiological saline solution.

Figure 18:
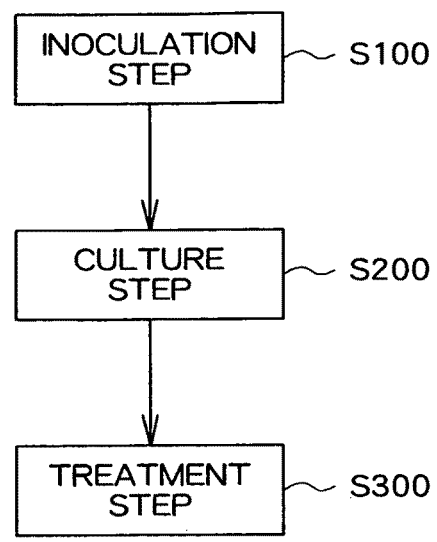
FIG. 18 is a flowchart illustrating main steps involved in a cell culture method according to the embodiment of the present invention.

FIG. 18 is a flow chart illustrating main steps included in the present method. As illustrated in FIG. 18, the present method includes steps of inoculating cells into the microwell group 20 of the instrument 1 (inoculation step S100), culturing the cells in the microwell group 20 (culture step S200), and subjecting the cells cultured in the microwell group 20 to a predetermined treatment (treatment step S300).

In the inoculation step S100, for example, a solution containing cells is injected into the macrowell 50 of the instrument 1 while the frame member 3 is being attached to the base member 2 as illustrated in FIGS. 3 and 4, thereby allowing the cells to be inoculated into one microwell group 20 corresponding to the macrowell 50. In this case, specifically, the instrument 1 in an attached state is left standing in a gas phase (air) in the sterile space for culture operation, such as a clean bench. Then, the operator pours the culture medium with the cells dispersed therein into the macrowell 50 of the instrument 1 using a pipette. As a result, the cells can be inoculated in each of a plurality of microwells 21 formed in the bottom 51 of the macrowell 50. In such an inoculation step S100, the amount of the cells and the volume of the solution required for the inoculation can be reduced to those corresponding to the capacity of the macrowell 50, and the cells can be thus reliably inoculated into the respective microwells 21.

In addition, for example, when a plurality of macrowells 50a to 50d are formed in the instrument 1 as illustrated in FIGS. 8 and 9, the cells may also be inoculated to each of the plurality of macrowells 50a to 50d under their respective different conditions with respect to one another. In other words, for example, different kinds of cells can be inoculated into different macrowells 50a to 50d, the cells can be inoculated at different densities into different macrowells 50a to 50d, or the cells can be inoculated using different culture mediums into different macrowells 50a to 50d with respect to one another.

In the culture step S200, for example, the base member 2 is detached from the frame member 3 when the cells have been inoculated into the instrument 1 in an attached state in the inoculation step S100. Then the cells can be cultured in the microwell group 20 of the instrument 1 in a separated state. In other words, for example, only the base member 2 from which the frame member 3 has been detached (the instrument 1 in a separated state) is placed in a predetermined culture vessel (for example, a plastic dish with a diameter of several centimeters, which is one commonly used for cell culture). The cells are then cultured in a state that the base member 2 is entirely immersed in the culture medium.

In the culture step S200, alternatively, the cell culture may be performed in the instrument 1 in an attached state without detaching the frame member 3 from the base member 2. Similarly, in this case, the instrument 1 is placed in a predetermined culture vessel. Then, the cells are cultured in the microwell group 20 of the instrument 1 entirely immersed in the culture medium.

Figure 19:
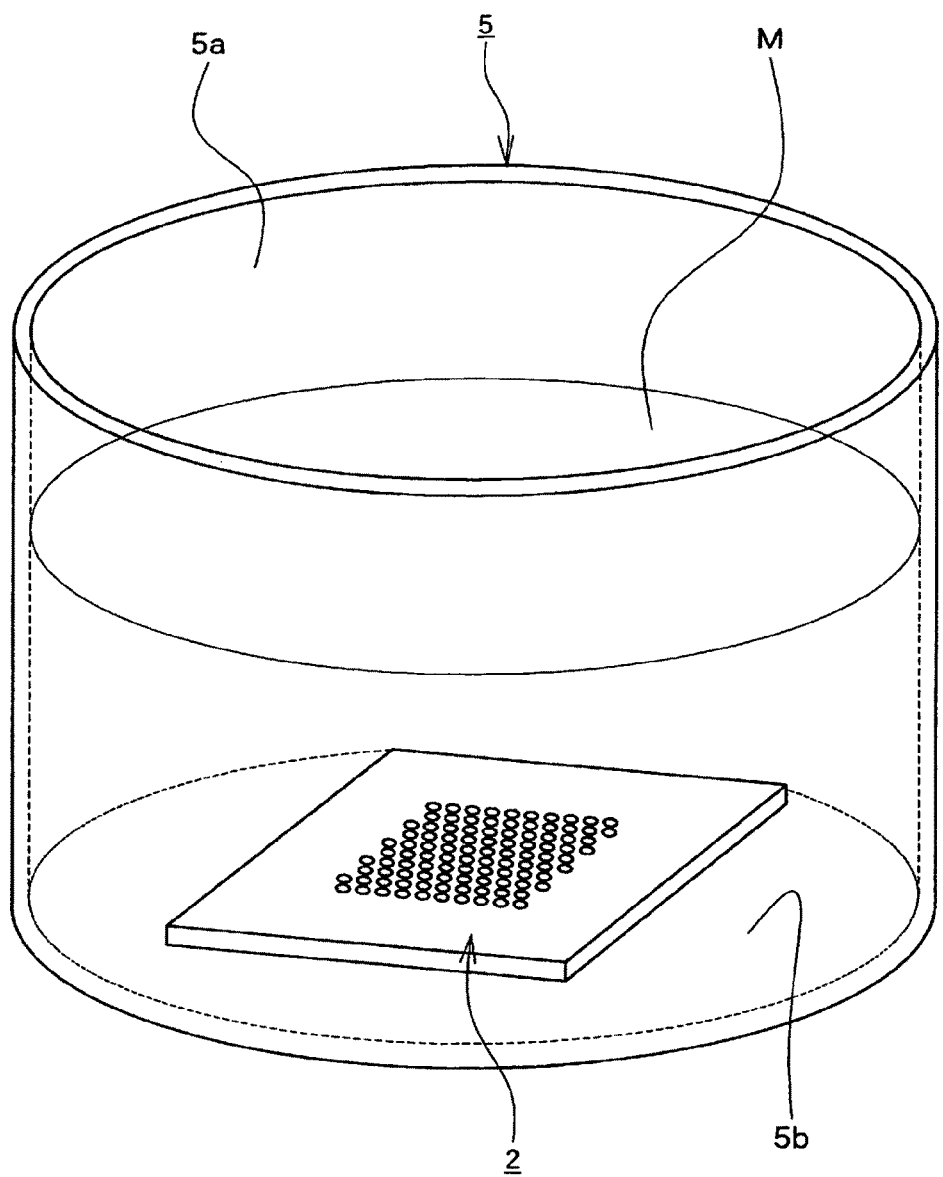
FIG. 19 is a perspective diagram illustrating an example of a culture state of the cell culture instrument according to the embodiment of the present invention.

FIG. 19 is an explanatory diagram illustrating an example in which the culture is carried out by immersing the entire instrument 1 in a separated state (the base member 2 from which the frame member 3 has been detached) in the culture medium M. In addition, FIG. 20 is an explanatory diagram illustrating an example in which the culture is carried out by immersing the entire instrument 1 in an attached state in the culture medium M.

Figure 20:
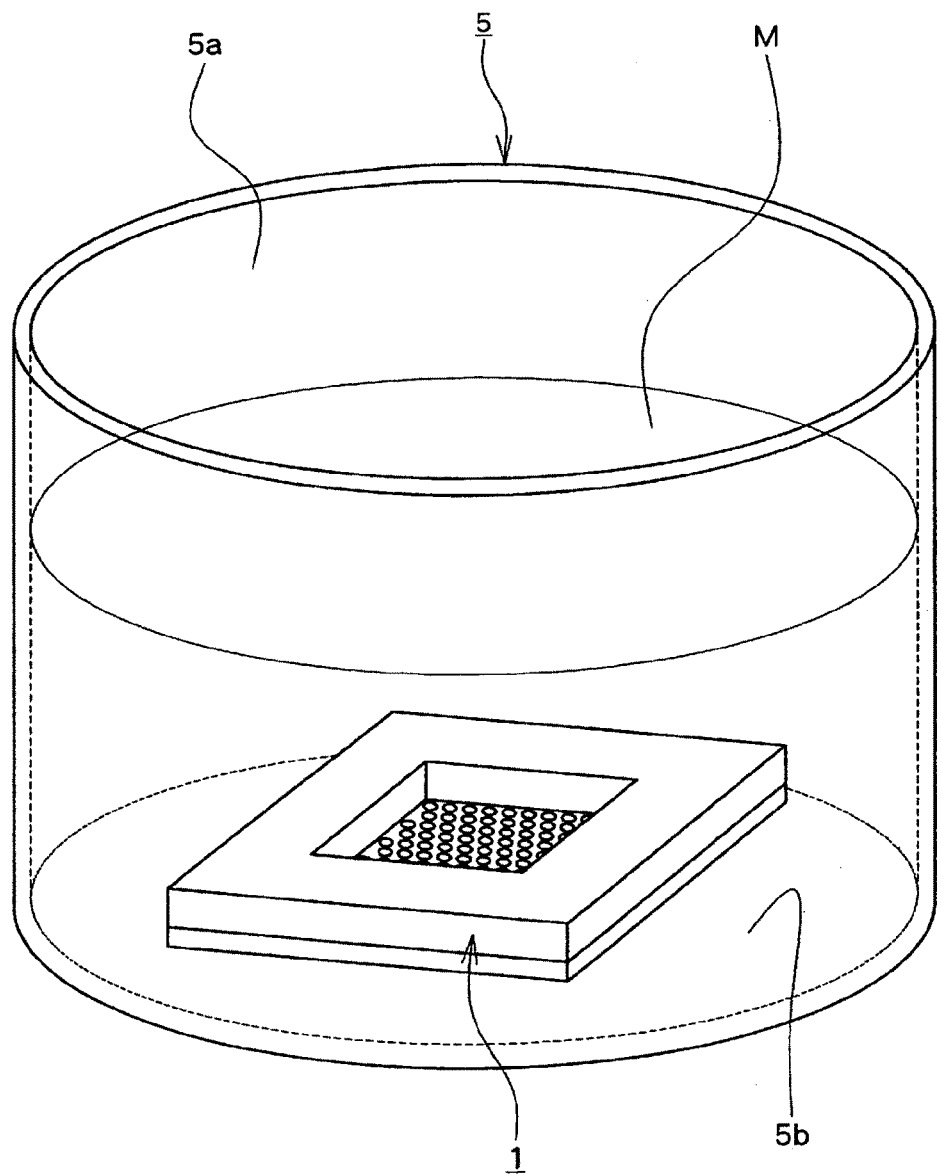
FIG. 20 is a perspective diagram illustrating another example of the culture state of the cell culture instrument according to the embodiment of the present invention.

As illustrated in FIGS. 19 and 20, in the case of culturing cells using the instrument 1, a culture vessel 5 which can house the entire instrument 1 can be used. The culture vessel 5 includes a culture portion 5a which can house the instrument 1. Then, the instrument 1 is placed on the bottom 5b in the culture portion 5a and the culture portion 5a is then filled with the culture medium M. As a result, the instrument 1 is held on the bottom 5b of the culture vessel 5 while being sunk in the culture medium M. Thus, the cells can be cultured in the respective microwells 21 of the instrument 1 housed in the culture vessel 5. Here, the culture vessel 5 used may be, for example, a plastic dish which is commonly used for cell culture.

Further, for example, when observing cells held in each microwell 21 by an optical device, such as a microscope, in the instrument 1 in an attached state, scattering of light may be caused by the frame member 3, which may be inconvenient in observation. Therefore, in the culture step S200, for example, it is preferred to detach the frame member 3 from the base member 2 to make the instrument 1 in a separated state to perform the microscopic observation of cells in the microwell 21. After the observation, the frame member 3 is attached to the base member 2 again and the culture of cells may be continued. Thus, in the instrument 1, the frame member 3 and the base member 2 are designed to be attachable to each other and also detachable from each other. Thus, the state of being attached and the state of being detached can be changed at any timing any number of times if required.

In the treatment step S300, for example, a predetermined solution is injected into the macrowell 50 of the cell-culturing instrument 1 in an attached state. Thus, the cells in one microwell group 20 corresponding to the macrowell 50 can be brought into contact with the predetermined solution. In this case, specifically, the instrument 1 in an attached state, where the cells are cultured in the microwell group 20, is left standing in a gas phase (air) in the sterile space for culture operation, such as a clean bench. Then, the operator recovers the culture medium from the macrowell 50 using a pipette and then pours a predetermined flesh solution into the macrowell 50. As a result, the cells held in each of a plurality of microwells 21 formed in the bottom 51 of the macrowell 50 can be brought into contact with the predetermined solution. In the treatment step S300, the volume of the solution required for the treatment can be reduced to one corresponding to the capacity of the macrowell 50, and the cells in the respective microwells 21 can be reliably brought into contact with the solution.

In addition, for example, when a plurality of macrowells 50a to 50d are formed in the instrument 1 as illustrated in FIGS. 8 and 9, different solutions can be injected into the respective macrowells 50a to 50d of the instrument 1 with respect to one another. In this case, the cells in a plurality of microwell groups 20a to 20d corresponding to a plurality of macrowells 50a to 50d can be brought into contact with the different solutions with respect to one another. In other words, the cells in the macrowells 50a to 50d can be brought into contact with the different solutions with respect to one another. Specifically, for example, a solution containing one of four kinds of different reagents may be injected to each of four macrowells 50a to 50d to bring the cells into contact with the different kinds of reagents with respect to the respective macrowells 50a to 50d.

Therefore, by using the instrument 1 including the base member 2 in which a plurality of microwell groups 20 are formed and the frame member 3 in which a plurality of window portions 40 are formed, the culture of cells can be simply performed under various conditions with reliability, for example, even if the number of cells that can be cultured is extremely small or the amount of a solution used for the treatment of cells or the amount of the reagent to be dissolved in the solution is extremely small.

For example, in the culture step S200, if a cell organoid is formed in each of the microwells 21, then the cell organoid can be subjected to a predetermined treatment in the treatment step S300. That is, when the whole bottom 22 of each of the microwells 21 is formed to be cellular non-adhesiveness and cell organoids are formed in each of the microwells 21, the cell organoids are held in suspension in a plurality of microwells 21. Thus, in the treatment step S300, a plurality of cell organoids can be simply and reliably collected from a plurality of microwells 21.

In this case, further, as illustrated in FIGS. 8 and 9, when cell organoids are formed in a plurality of macrowells 50a to 50d in the instrument 1, those cell organoids can also be selectively collected from part of the plurality of the macrowells 50a to 50d, for example, from only one macrowell 50a in the instrument 1 in an attached state.

In addition, for example, when the central portion of the bottom 22 of each microwell 21 is provided with a cellular adhesive first region and the peripheral portion surrounding the first region serving as a cellular non-adhesive second region, a cellar organoid being attached to the first region of the bottom 22 can be formed in the microwell 21. In this case, in the treatment step S300, each cell organoid being attached to each bottom 22 can be subjected to a predetermined treatment, such as bringing into contact with a predetermined solution.

In this case, further, if a cell organoid is formed in each of a plurality of macrowells 50a to 50d of the instrument 1 as illustrated in FIGS. 8 and 9, the cell organoid attached on the bottoms 22 of each of the plurality of macrowells 50a to 50d can be contacted to different solutions with respect to one another.

Figure 21:
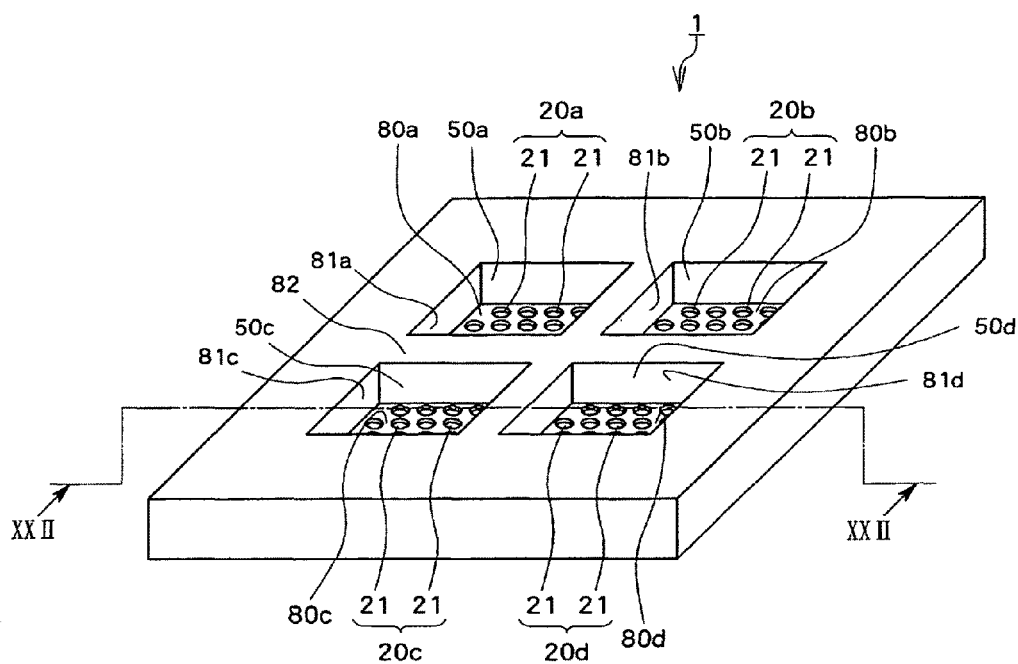
FIG. 21 is a perspective diagram illustrating another example of the cell culture instrument according to the embodiment of the present invention.
Figure 22:
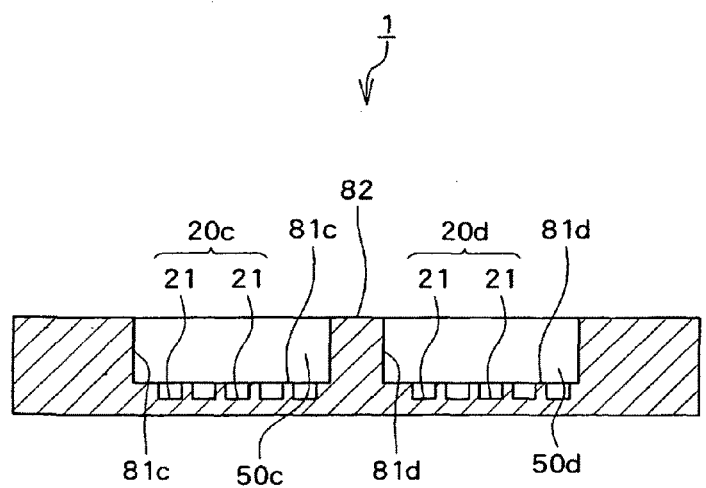
FIG. 22 is a cross-sectional view of the instrument 1 taken along the line XXII-XXII illustrated in FIG. 21.

FIGS. 21 and 22 are explanatory diagrams and views illustrating another example of the instrument 1. FIG. 21 is a perspective diagram of the instrument 1 and FIG. 22 is a cross-sectional view of the instrument 1 taken along a plane corresponding to the line XXII-XXII illustrated in FIG. 21.

The instrument 1 of the example illustrated in FIGS. 21 and 22 includes base portions 80a to 80d corresponding to the base member 2 in the above-mentioned example, and frame portions 81a to 81d corresponding to the frame member 3 in the above-mentioned example. Those base portions 80a to 80d and frame portions 81a to 81d are integrally formed so that they cannot be detached from each other. In addition, the base portions 80a to 80d and the corresponding frame portions 81a to 81d form macrowells 50a to 50d which can hold solutions therein.

More specifically, the base portions 80a to 80d correspond to the bottoms 51a to 51d of the macrowells 50a to 50d in the example illustrated in FIGS. 6 to 9, and the frame portions 81a to 81d correspond to the inner walls 41a to 41d of the window portions 40a to 40d in the example illustrated in FIGS. 6 to 9. Microwell groups 20a to 20d are formed in the respective base portions 80a to 80d in a one-by-one relationship. The frame portions 81a to 81d are vertically arranged around their respective microwell groups 20a to 20d, respectively. In addition, the instrument 1 includes a partition portion 82 formed in cross shape to partition four macrowells 50a to 50d from one another.

Further, in the instrument 1 having the base portions 80 and the frame portions 81 and being integrally formed, just as in the case with the above-mentioned example, the formation of the macrowell 50 leads to prevent minute microwells 21 from drying out. Therefore, a desired cell culture operation can be simply and reliably performed on every microwell group 20. In addition, a plurality of microwell groups 20a to 20d may be subjected to different treatments with respect to one another.

The materials of the instrument 1 in which the base portions 80a to 80d and the frame portions 81a to 81d are integrally formed may be the same materials as those used for the above-mentioned base member 2 and the above-mentioned frame member 3. That is, one material may be used alone, or a plurality of materials may be used in combination, each selected from the group consisting of, for example: synthetic resins such as polystyrene, polyethylene, polypropylene, polycarbonate, polyamide, polyacetal, polyester (such as polyethylene terephthalate), polyurethane, polysulfone, polyacrylate, polymethacrylate (such as PMMA), and polyvinyl; silicon-based resins such as PDMS; synthetic rubber such as EPDM; natural rubber; glass; ceramic; and metal materials such as stainless steel.

In addition, the material forming the instrument 1, in particular, the material forming the portion where the microwell group 20 is formed may be preferably a transmissive material, of the materials described above, from a standpoint of, for example, the convenience for observing cells cultured in the microwell group 20 by optical means such as a microscope. In other words, in this embodiment, the instrument 1 may be formed of a synthetic resin or glass, the whole or part of which is transmissive, for example.

Any processing method selected depending on the purpose can be used for the formation of the microwells 21. In other words, for example, punching processing using machining center or the like, optical micro-processing using laser or the like, etching processing, emboss processing, or the like, can be used for forming the microwells 21 in part of previously formed base portions 80a to 80d of instrument 1. In this case, for example, the instrument 1 may also be manufactured by forming microwells 21 on the bottom of a commercially-available plastic dish formed of a transmissive resin, such as polystyrene, by the above-mentioned processing. In addition, for example, injection molding, press molding, stereo-lithography, or the like can form microwells 21 in part of each of the base portions 80a to 80d simultaneously with the formation of the instrument 1 in which the base portions 80a to 80d and the frame portions 81a to 81d are integrally formed.

As described above, in particular, the instrument 1 of the present invention allows a cell culture operation to be simply and reliably carried out using rare cells and rare reagents. Therefore, the instrument 1 can be expected as a very useful tool in various industrial applications including drug designs, regenerative medicine, basic research, and so on, in which cultured cells are used.

Next, a specific example of the present method using the instrument 1 is described.

EXAMPLE 1

By using instruments 1 as illustrated in FIGS. 1 to 4, in the inoculation step S100, an efficiency of holding cells in the microwell group 20 with respect to a case where cells were inoculated in the instrument 1 of an attached state was compared with one with respect to a case where cells were inoculated in the instrument 1 of a separated state. In other words, within a rectangular area of 10 mm×10 mm on the surface of a flat plate (24 mm×24 mm, 400 μm in thickness) formed of PMMA, 1020 circular microwells 21 of 300 μm in diameter and 200 μm in depth were formed by a punching process using a machining center (bench-top NC micro-processing machine, manufactured by PMT CORPORATION). The plural microwells 21 were regularly arranged so that the distance between the centers of the circles of the respective opening portions 24 of the respective microwells 21 and the bottoms 22 and the distance between the centers of the circles of respective bottoms 22 could be 330 μm. Next, by subjecting the resultant to a sputtering process using a sputtering system (E-1030, manufactured by Hitachi, Co., Ltd.), a platinum (Pt) thin film (6 nm in thickness) is formed on the surface.

Consequently, the base member 2 as illustrated in FIGS. 1 to 4 was produced. In other words, in the 10 mm×10 mm rectangular area of the upper surface 11 of the base member 2, one microwell group 20 including 1020 microwells 21 of 200 μm in depth was formed with the opening portion 24 and the bottom 22 of the microwell 21 being circular with a diameter of 300 μm.

Further, an ethanol solution containing a synthetic polymer (chemical formula: $CH_3(CH_2CH_2)_nSH$, manufactured by NOF CORPORATION) with cellular non-adhesiveness having a polyethylene glycol (PEG) chain with a molecular weight of 30,000 at a concentration of 5 mM was injected into each of the microwells 21 to form a chemical bonding between a thiol group of the cellular non-adhesive polymer and the platinum surface of the bottom 22 of each microwell 21 under nitrogen atmosphere to immobilize the cellular non-adhesive polymer on the bottom 22. Subsequently, the entire first substrate portion 10 was sufficiently washed with an ethanol solution to remove the excessive cellular non-adhesiveness polymer. Then, the first substrate portion 10 was immersed in ethanol for 10 minutes, followed by being subjected to sterilization by UV irradiation for about 30 minutes. The bottom 22 of each microwell 21 thus formed was entirely of cellular non-adhesiveness.

On the other hand, a window portion 40 was formed as a rectangular through-hole (10 mm×10 mm) in a flat plate (20 mm×20 mm, 2.2 mm in thickness) formed of PDMS so that the window portion 40 could house the microwell group 20 of the first substrate portion 10, thereby forming a frame member 30 as illustrated in FIGS. 1 to 4. In other words, first, 13 mL of a PDMS solution (Sylgard 184, manufactured by Dow Corning, Co., Ltd.) prepared by mixing a PDMS prepolymer with a hardening agent at a volume ratio of 10:1 was poured into a plastic dish of 90 mm in diameter and then left standing for two days at room temperature to harden the solution. Subsequently, the hardened PDMS disk was removed from the dish and then cut into a PDMS frame member 3 of the above-mentioned shape using a scalpel. The frame member 3 was entirely formed of PDMS. Thus, in the case of the instrument in an attached state, constructed by pressing the lower surface 31 of the frame member 3 against the upper surface 11 of the base member 2, the lower surface 31 and the upper surface 11 could be easily and reliably adhered to each other. Consequently, an instrument 1 in which one macrowell 50 capable of holding the solution was formed as illustrated in FIGS. 3 and 4 could be obtained.

In addition, under the first condition, as illustrated in FIG. 20, the instrument 1 in an attached state is placed in a plastic dish (culture vessel 5) of 35 mm in diameter. Into the macrowell 50 (10 mm×10 mm×2.2 mm) of the instrument 1, 0.25 mL of a cell dispersion solution prepared by dispersing HepG2 cells (the Institute of Physical and Chemical Research/bio-resource center) in a culture medium (Williams medium E, added with 10% fetal bovine serum) at a density of $4 \times 10^5$ cells/mL was poured. In other words, $1 \times 10^5$ HepG2 cells were inoculated in one macrowell 50. After two hours passed from the inoculation, cells held in the microwell group 20 in the macrowell 50 were collected by pipetting and the content of deoxyribonucleic acid (DNA) in the collected cells was then quantified. The DNA quantification was performed by the method using 4'6-diamidino-2-phenylindole (DAPI). From the results of the DNA quantification, the ratio of the number of cells actually held in the microwell 21 to the total number of the cells used in the inoculation was calculated as a cell-immobilization rate (%).

On the other hand, under the second condition, as illustrated in FIG. 19, the instrument 1 in a separated state (i.e., only the base member 2) was placed in a plastic dish (culture vessel 5) of 35 mm in diameter. Into the plastic dish, 2 mL of a cell dispersion solution prepared by dispersing HepG2 cells in the above-mentioned culture medium at a density of $4 \times 10^5$ cells/mL was poured. In other words, $8 \times 10^5$ HepG2 cells were inoculated in the plastic dish. It should be noted that, at this time, the entire base member 2 was immersed in the culture medium in the culture vessel 5. Further, just as in the case of the first condition, the cells held in the microwell group 20 were collected and then subjected to the DNA quantification to calculate a cell-immobilization rate (%).

Consequently, in contrast to a cell immobilization rate of about 15% under the above-mentioned second condition, the cell immobilization rate was about 100% under the above-mentioned first condition. In other words, it was confirmed that cells could be easily and reliably held in the microwell group 20 by inoculating the cells in the instrument in an attached state in which the frame member 3 is being attached to the base member 2.

EXAMPLE 2

By using an instrument 1 manufactured in the same way as that of the above-mentioned Example 1, the inoculation step S100 performs a comparison between the case in which cells were inoculated in the instrument 1 in an attached state and the case in which cells were inoculated in the instrument 1 in a separated state with respect to a variation in the number of cells held in each of a plurality of microwells 21.

More specifically, under the first condition, as illustrated in FIG. 20, the instrument 1 in an attached state is placed in a plastic dish of 35 mm in diameter. Into the macrowell 50 (10 mm×10 mm×2.2 mm) of the instrument 1, 0.25 mL of a cell dispersion solution prepared by dispersing HepG2 cells in a culture medium (Williams medium E, added with 10% fetal bovine serum) at a density of $4 \times 10^5$ cells/mL was poured. After two hours passed from the inoculation, the number of cells piled on the bottom 22 of each of 60 microwells 21 formed near the center of the instrument 1 was counted under a phase contrast microscope.

On the other hand, under the second condition, as illustrated in FIG. 19, the instrument 1 in a separated state (i.e., only the base member 2) was placed in a plastic dish of 35 mm in diameter. Into the plastic dish, 2 mL of a cell dispersion solution prepared by dispersing HepG2 cells in the above-mentioned culture medium at a density of $4 \times 10^5$ cells/mL was poured. Then, after two hours from the inoculation, the number of cells piled on the bottom 22 of each of 60 microwells 21 formed at the same position as that under the above-mentioned first condition was counted under a phase contrast microscope.

Consequently, the number of cells held in one microwell 21 was $68.2 \pm 13.4$ (arithmetic average±standard deviation) under the first condition and $66.9 \pm 16.9$ (arithmetic average±standard deviation) under the second condition. In other words, it was confirmed that the inoculation of cells in the instrument 1 in an attached state in which the frame member 3 was attached to the base member 2 could reduce a variation in the number of cells held in each microwell 21.

EXAMPLE 3

An instrument 1 prepared in a manner similar to that in the above-mentioned example 1 was used for the formation of a cell organoid in each of the microwells 21. Further, in the culture step S200, a comparison was made between the case in which the cell organoids held in the instrument 1 in an attached state was microscopically observed and the case in which the cell organoids held in the instrument 1 in a separated state was microscopically observed with respect to the clearness of the observation.

That is, HepG2 cells were inoculated in each microwell 21 of the instrument 1 and then cultured for 10 days so that one spherical cell organoid (HapG2 spheroid) as a three-dimensional aggregate of the HepG2 cells was formed in each microwell 21. Here, a Williams medium E added with 10% fetal bovine serum was used as the culture medium and $2 \times 10^5$ HepG2 cells were inoculated in each macrowell 50. Subsequently, the HepG2 spheroid cultured for 10 days was observed in each microwell 21 in the instrument 1 in an attached state or a separated state under a phase contrast microscope.

Figure 23:
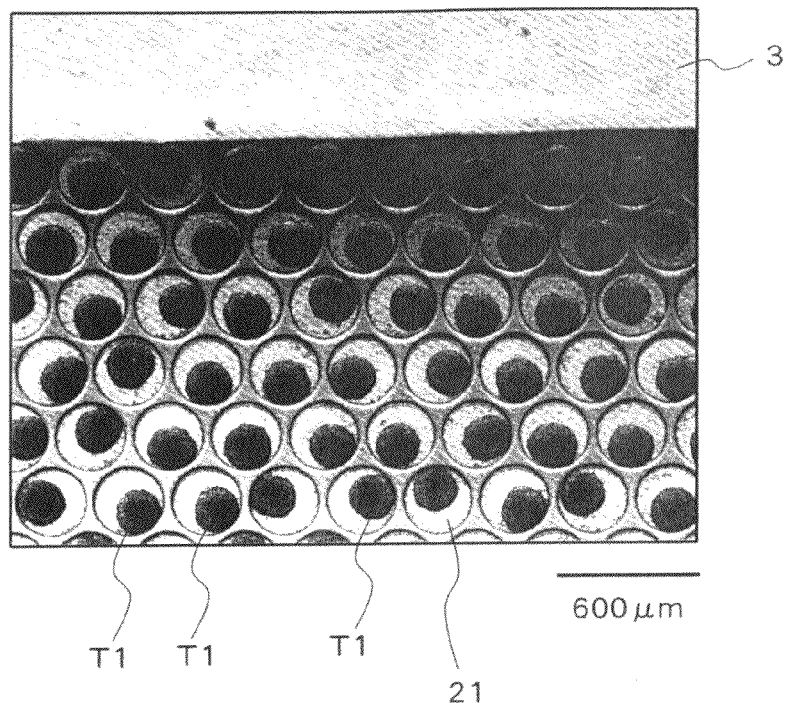
FIG. 23 is a microphotograph showing an example of cell organoids formed in the cell culture instrument according to the embodiment of the present invention.
Figure 24:
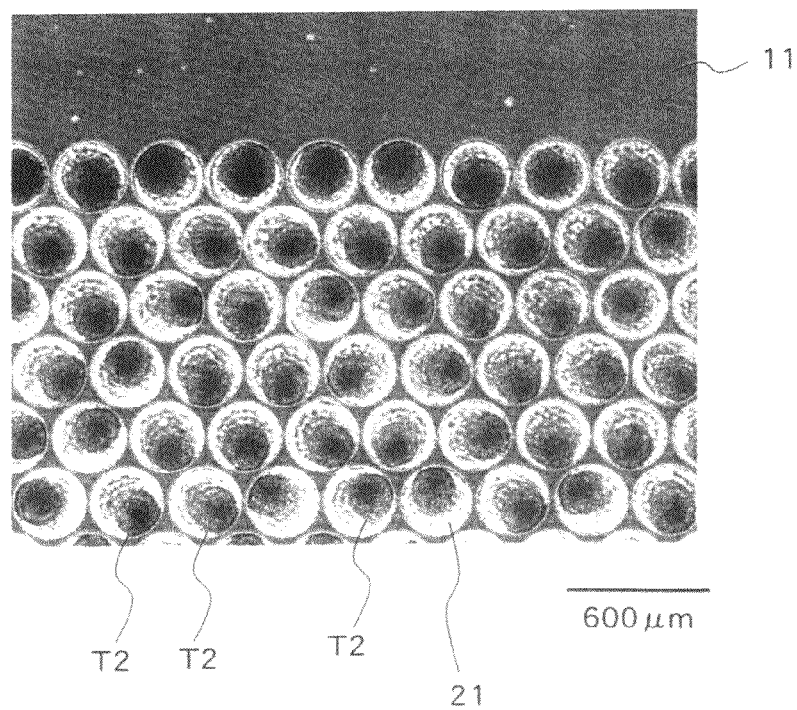
FIG. 24 is a microphotograph showing another example of the cell organoids formed in the cell culture instrument according to the embodiment of the present invention.

FIG. 23 represents a phase contrast micrograph of the HepG2 spheroid T1 formed in the microwell 21 on the end portion of the microwell group 20 near the frame member 3 of the instrument 1 in an attached state. In a manner similar to FIG. 23, on the other hand, FIG. 24 represents a phase contrast micrograph of the HepG2 spheroid T2 formed in the microwell 21 on the end portion of the microwell group 20 near the frame member 3 in the instrument 1 in a separated state. As illustrated-in FIG. 23, in the instrument 1 in an attached state, part of the HepG2 spheroid T1 in the microwell 21 of the microwell group 20, which was close to the frame member 3, was not clearly observed. In contrast, as illustrated in FIG. 24, in the instrument 1 in a separated state, the HepG2 spheroid T2 in each of microwells 21 was clearly observed in the entire area of the microwell group 20. That is, it was confirmed that the observation of cells or cell organoids in the respective microwells 21 of the instrument 1 could be preferably performed in the instrument in a separated state where the frame member 3 was being detached from the base member 2.

EXAMPLE 4

In a manner similar to that in the above-mentioned example 1, two kinds of the instruments 1 (hereinafter, referred to as a "first instrument 1" and a "second instrument 1") in which the bottom 22 of each microwell 21 was cellular non-adhesiveness. In the first instrument 1, one microwell group 20 including regularly arranged 572 microwells 21 of 200 μm in depth was formed in the 10 mm×10 mm rectangular area of the upper surface 11 with the opening portion 24 and the bottom 22 of the microwell 21 being circular with a diameter of 300 μm, and a center distance being 440 μm. In the second instrument 1, one microwell group 20 including regularly arranged 572 microwells 21 of 260 μm in depth was formed in the 10 mm×10 mm rectangular area of the upper surface 11 with the opening portion 24 and the bottom 22 of the microwell 21 being circular with a diameter of 400 μm, and a center distance being 440 μm. The formation of cell organoids in the respective microwells 21 of the first instrument 1 and the formation of cell organoids in the respective microwells 21 of the second instrument 1 are carried out, respectively.

That is, as illustrated in FIG. 20, the first instrument 1 in an attached state is placed in a plastic dish (culture vessel 5) of 35 mm in diameter. Next, a cell dispersion solution in which mouse ES cells (Dainippon Sumitomo Pharma) were being dispersed was injected into the macrowell 50 of the first instrument 1 to inoculate the mouse ES cells into the respective microwells 21. Subsequently, 2.0 mL of the culture medium was further added to the culture vessel 5 and the culture was then performed for five days while the entire first instrument 1 in an attached state was immersed in the culture medium. Consequently, one spherical cell organoid (embryoid) could be formed as a three-dimensional aggregate of the mouse ES cells in each microwell 21. The culture medium used was a DMEM culture medium containing 15% fetal bovine serum, 1% nucleoside, 1% nonessential amino acid, 1% 2-melcaptoethanol, and 1% glutamine and $1\times10^5$ mouse ES cells were inoculated into one macrowell 50 of the first instrument 1. Likewise, mouse neural stem cells (provided from National Hospital Organization Osaka National Hospital) were inoculated into the respective microwells 21 in the second instrument 1 placed in the culture vessel 5. After the culture for five days, one spherical cell organoid (neurosphere) was formed as a three-dimensional aggregate of the mouse neural stem cells in each microwell 21. The culture medium used was a DMEM/F12 culture medium containing 1% N-2 supplement, 20 ng/mL of Human recombinant EGF, and 20 ng/mL of Human recombinant bFGF, and $1\times10^5$ mouse neural stem cells were inoculated into one macrowell 50 of the second instrument 1.

In addition, as a control group, the cellular non-adhesive polymer, which was the same as one immobilized on the bottom 22 of each microwell 21 of the above-mentioned first and second instrument 1 and 2, was immobilized on the whole bottom of a plastic dish of 35 mm in diameter (tissue culture dish, manufactured by Becton, Dickinson and Company). Then, mouse ES cells or mouse neural stem cells were cultured in the culture dish for five days. Here, with respect to the mouse ES cells, the culture medium used was a DMEM culture medium containing 15% fetal bovine serum, 1% nucleoside, 1% nonessential amino acid, 1% 2-melcaptoethanol, and 1% glutamine, and $4\times10^5$ cells were inoculated into one culture dish. With respect to the mouse neural stem cells, the culture medium used was a DMEM/F12 culture medium containing 1% N-2 supplement, 20 ng/mL of Human recombinant EGF, and 20 ng/mL of Human recombinant bFGF, and $1\times10^5$ cells were inoculated into one culture dish.

Subsequently, the cell organoids formed in the respective microwells 21 of the instrument 1 or the respective control culture dishes at the fifth day of culture were observed under a phase contrast microscope. Then, the distributions of the size of 100 embryoids or neurospheres were measured.

Figure 25:
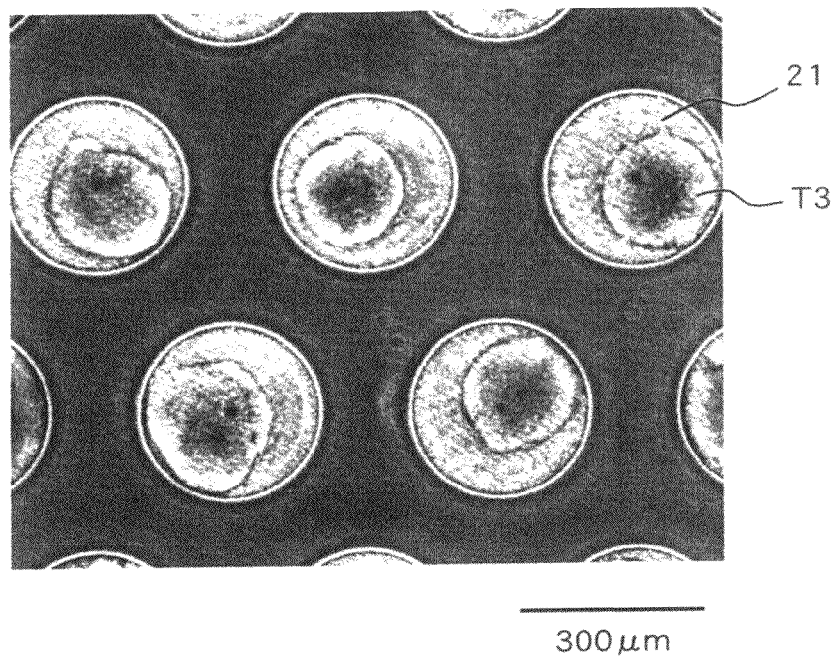
FIG. 25 is a microphotograph showing an example of embryoids formed in the cell culture instrument according to the embodiment of the present invention.
Figure 26:
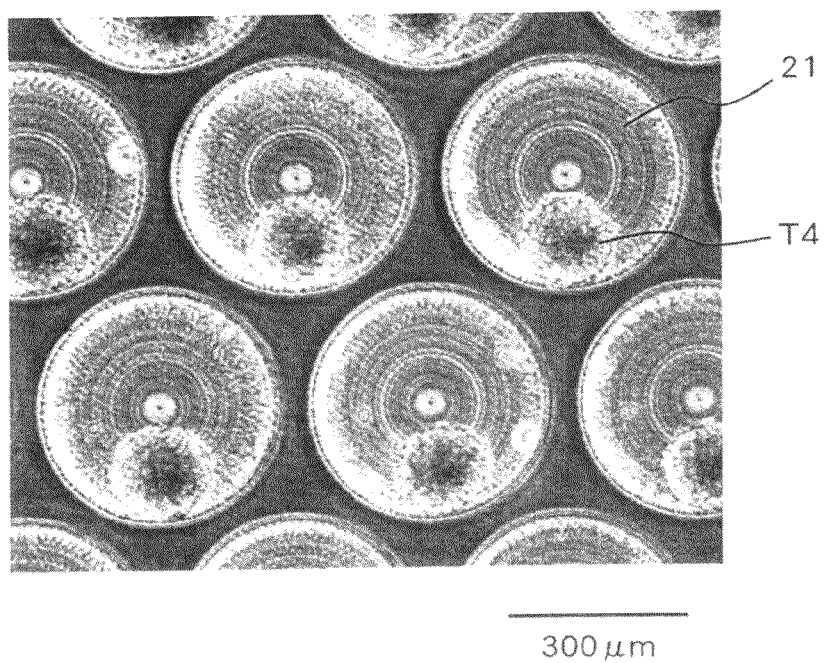
FIG. 26 is a microphotograph showing an example of a neurospheres formed in the cell culture instrument according to the embodiment of the present invention.

Consequently, as illustrated in FIG. 25, one spherical embryoid T3 was formed in each microwell 21 of the instrument 1 in which the mouse ES cells had been inoculated. In addition, as illustrated in FIG. 26, one spherical neurosphere T4 was formed in each microwell 21 of the instrument 1 in which the mouse neural stem cells had been inoculated. Those embryoids and neurospheres remained suspended without being adhered on the bottoms 22 of the respective microwells 21, respectively.

Figure 27:
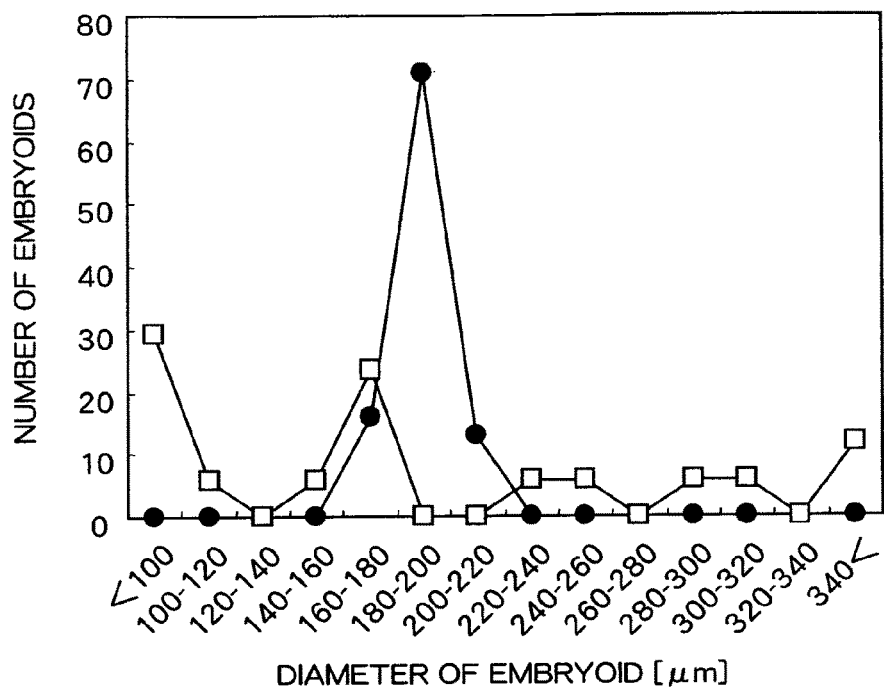
FIG. 27 is an explanatory view illustrating an example of a particle size distribution of the embryoids formed in the cell culture instrument according to the embodiment of the present invention.
Figure 28:
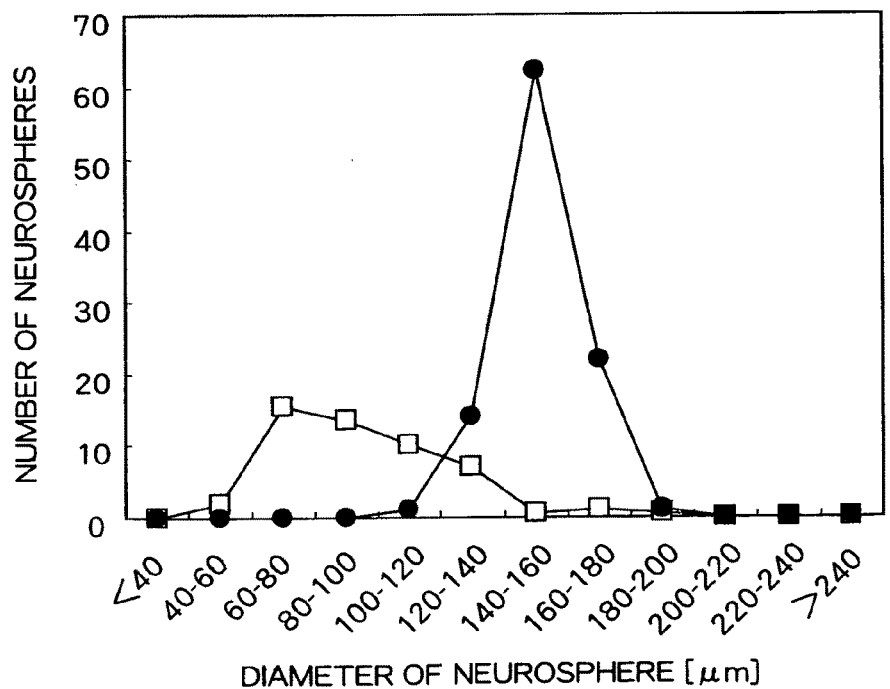
FIG. 28 is an explanatory view illustrating an example of a particle size distribution of the neurospheres formed in the cell culture instrument according to the embodiment of the present invention.

FIG. 27 represents the distribution of the diameter of the embryoids formed in the respective microwells 21 of the instrument 1 or the respective control culture dishes on the fifth day of the culture. FIG. 28 represents the distribution of the diameter of the neurospheres formed in the respective microwells 21 of the instrument 1 or the respective control culture dishes on the fifth day of the culture. In each of FIGS. 27 and 28, the horizontal axis represents the diameter (μm) of the cell organoid and the vertical axis represents the number (N) of the cell organoids of the respective diameters. In addition, the-closed circle symbol represents a measured value for the cell organoid formed in the microwell group 20 of the instrument 1. The opened square symbol represents a measured value for the cell organoid formed in the control culture dish. As illustrated in FIGS. 27 and 28, cell organoids of various diameters were formed in the control culture dish. In contrast, cell organoids of uniform diameter were formed in the microwell group 20 of the instrument 1. That is, by culturing the mouse ES cells in the microwell group 20 of the first instrument 1, one embryoid with diameters in the range of 140 μm to 240 μm was formed in each of the microwells 21 without being adhered on the bottom 22. In addition, by culturing the mouse neural stem cells in the microwell group 20 of the second instrument 1, one neurosphere with diameters in the range of 120 μm to 200 μm was formed in each of the microwells 21 without being adhered on the bottom 22.

EXAMPLE 5

First, within a rectangular area of 10 mm×10 mm on the surface of a flat plate formed of PMMA (24 mm×24 mm, 200 μm in thickness), 672 circular through-holes of 300 μm in diameter were formed by a punching process using a machining center (bench-top NC micro-processing machine, manufactured by PMT CORPORATION). The circular through-holes were regularly arranged so that the distance between the centers of their circles could be 400 μm. Next, another PMMA flat plate (24 mm×24 mm, 200 μm in thickness), which was independently formed without any through-hole, was attached to the one-side surface of the PMMA flat plate, where the circular through-holes were formed, by thermo-compression bonding (106° C., 2 hours).

Consequently, the base member 2 as illustrated in FIGS. 1 to 4 was produced. Namely, in the 10 mm×10 mm rectangular area of the upper surface 11 of the base member 2, one microwell group 20 including regularly arranged 672 microwells 21 of 200 μm in depth was formed with the opening portion 24 and the bottom 22 of the microwell 21 being circular with a diameter of 300 μm, and a center distance being 400 μm. Next, by subjecting the resultant to a sputtering process using a sputtering system (E-1030, manufactured by Hitachi, Co., Ltd.) to form a platinum (Pt) thin film (6 nm in thickness) on the bottom 22 of each microwell 21.

On the other hand, a PDMS stamp provided with a plurality of cylindrical protrusions of 200 μm in diameter, 200 μm in length, and 400 μm in center distance, where the tip of each of them had a cylindrical protrusion of 100 μm in diameter and 70 μm in length was formed by molding. Then, a microcontact printing process using the stamp was carried out to form a cellular adhesive first region on the bottom 22 of each microwell 21. That is, the tips of the respective cylindrical protrusions of the stamp were dipped into an aqueous solution containing collagen (Cellmatrix Type I-C, manufactured by Nitta Gelatin Inc.) as a cellular adhesive protein. Subsequently, the position of each cylindrical protrusion was pressed against the position near the center of the bottom 22 of each microwell 21 deposited with the above-mentioned platinum under a phase contrast microscopic observation to apply the collagen applied on the tip of each cylindrical protrusion to the vicinity of the center of the bottom 22. Consequently, one first region with cellular adhesiveness with a diameter of about 100 μm was formed near the center of the bottom 22 of each microwell 21 of 300 μm in diameter.

Further, portions other than the first region of the bottom 22 were made cellular non-adhesive. That is, an ethanol solution containing a cellular non-adhesive synthetic polymer (chemical formula: $CH_3(CH_2CH_2)_nSH$, manufactured by NOF CORPORATION) having a cellular non-adhesive PEG chain with a molecular weight of 5000 or 10,000 at a concentration of 5 mM was injected into each microwell 21 after the formation of the first region. Then, it was left standing for a predetermined time under nitrogen atmosphere to immobilize the cellular non-adhesive polymer on the periphery of the first region of the bottom 22 of each microwell 21.

In each microwell 21 having the bottom 22 with both the cellular adhesive first region and the cellular non-adhesive second region formed as described above, primary rat hepatocytes or mouse ES cells (Dainippon Sumitomo-Pharma) were inoculated. After the culture for five days, one spherical cell organoid (hepatocyte spheroid) or one spherical embryoid was formed as a three-dimensional aggregate of the mouse neural stem cells in each microwell 21. Here, the primary, rat hepatocytes were cultured using the instrument 1 in which the cellular non-adhesive polymer having a-PEG chain with a molecular weight of 5000 was immobilized on the second region of each microwell 21. In addition, the mouse ES cells were cultured using the instrument 1 in which the cellular non-adhesive polymer having a PEG chain with a molecular weight of 10,000 was immobilized on the second region of each microwell 21. In addition, with respect to the primary rat hepatocytes, the culture medium used was a serum-free DMEM culture medium supplemented with 60 mg/L of proline, 50 μg/L of EGF, 10 mg/L of insulin, 7.5 mg/L of hydrocortisone, 0.1 μM of copper sulfate pentahydrate, 3 μg/L of selenic acid, 50 pM of zinc sulfate heptahydrate, 50 μg/L of linoleic acid, 58.8 mg/L of penicillin, 100 mg/L of streptomycin, 1.05 g/L of sodium bicarbonate, and 1.19 g/L of HEPES, and the cells were inoculated into the macrowell 50, which was only one formed in the instrument 1, at a density of $1.7 \times 10^5$ cells/cm². On the other hand, with respect to the mouse ES cells, the culture medium used was a DMEM culture medium containing 15% fetal bovine serum, 1% nucleoside, 1% nonessential amino acid, 1% 2-melcaptoethanol, and 1% glutamine, and the cells were inoculated into the macrowell 50, which was only one formed in the instrument 1, at a density of $1 \times 10^5$ cells/cm².

In addition, as a control group for primary rat hepatocytes, primary rat hepatocytes were cultured for five days in a plastic dish (Primaria, manufactured by Becton, Dickinson and Company) of 35 mm in diameter, which had been considered suitable for the formation of hepatocyte spheroids. As a control group for mouse ES cells, the cellular non-adhesive polymer, which was the same as one immobilized on the bottom 22 of each microwell 21, was immobilized on the whole bottom of a plastic dish (tissue culture dish, manufactured by Becton, Dickinson and Company) of 35 mm in diameter. Then, mouse ES cells were cultured in the culture dish for five days.

Subsequently, the cell organoids formed in the respective microwells 21 of the instrument 1 or the respective control culture dishes at the fifth day of culture were observed under a phase contrast microscope. Then, the distribution of the size of 100 hepatocyte spheroids or embryoids were measured.

Figure 29:
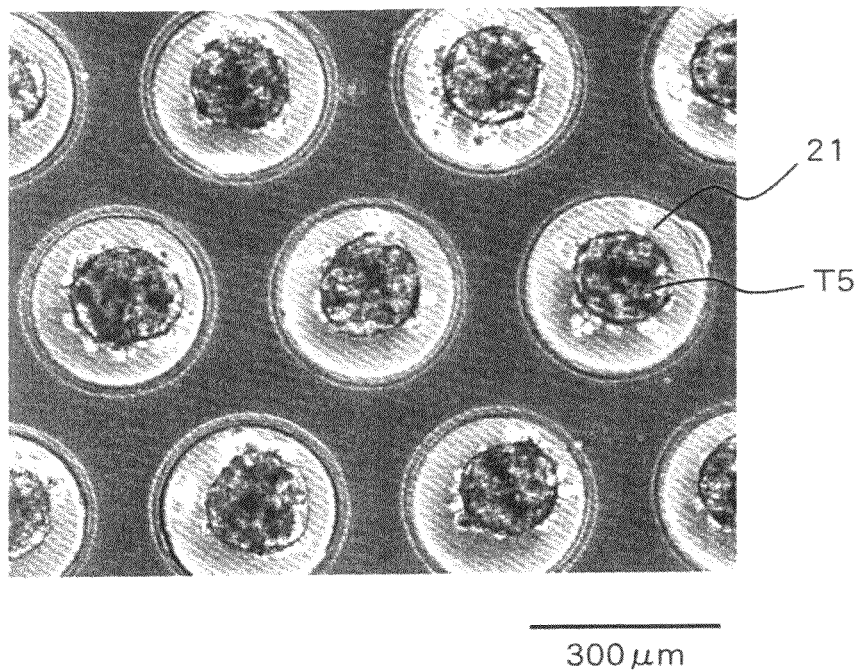
FIG. 29 is a microphotograph showing an example of hepatocyte spheroids formed in the cell culture instrument according to the embodiment of the present invention.
Figure 30:
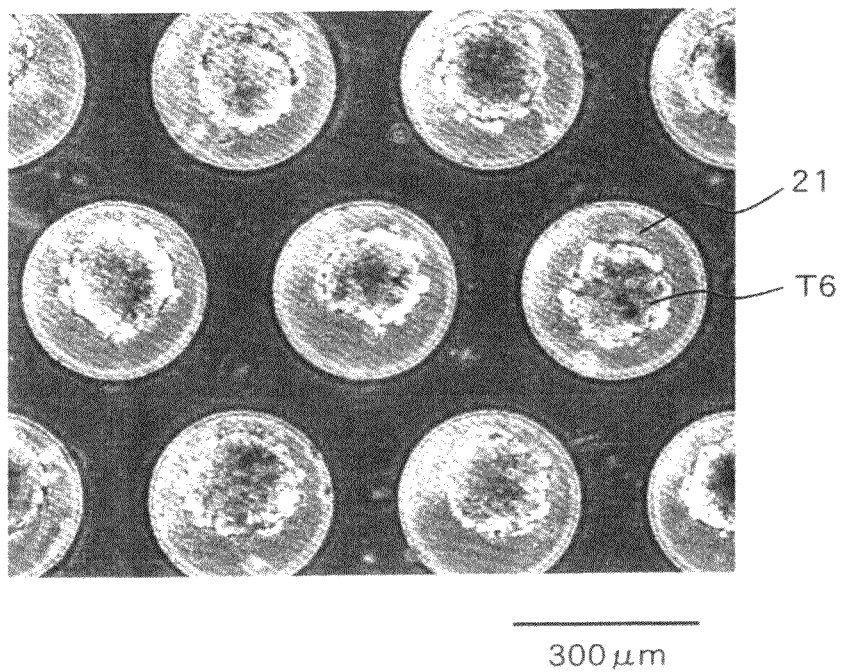
FIG. 30 is a microphotograph showing another example of the embryoids formed in the cell culture instrument according to the embodiment of the present invention.

Consequently, as illustrated in FIG. 29, one spherical hepatocyte spheroid T5 was formed in each microwell 21 of the instrument 1 in which the primary rat hepatocytes had been inoculated. In addition, as illustrated in FIG. 30, one spherical embryoid T6 was formed in each microwell 21 of the instrument 1 in which the mouse ES cells had been inoculated. Those hepatocyte spheroids and embryoids remained attached to the first regions of the bottoms 22 of the respective microwells 21, respectively.

Figure 31:
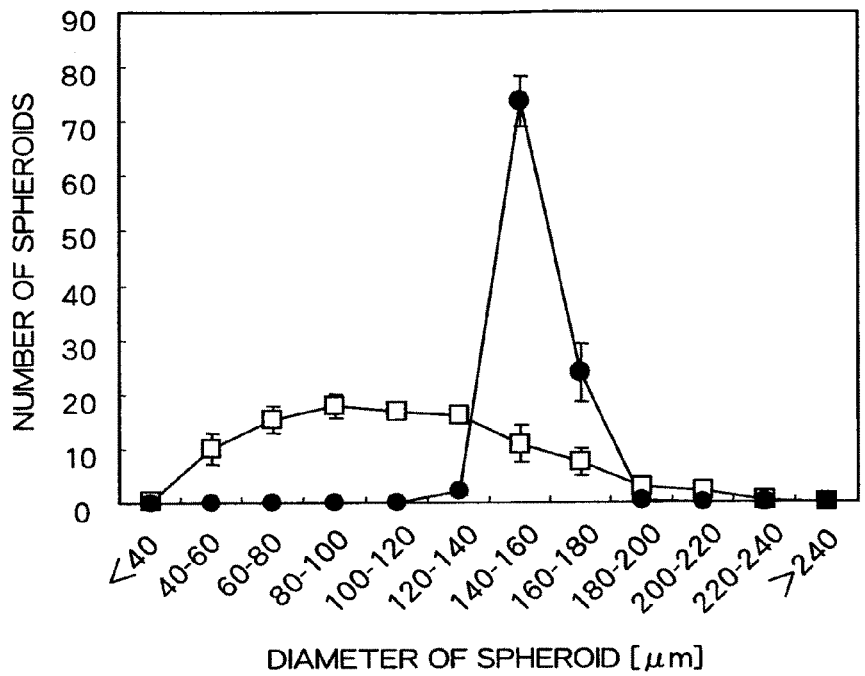
FIG. 31 is an explanatory view illustrating an example of a particle size distribution of the hepatocyte spheroids formed in the cell culture instrument according to the embodiment of the present invention.
Figure 32:
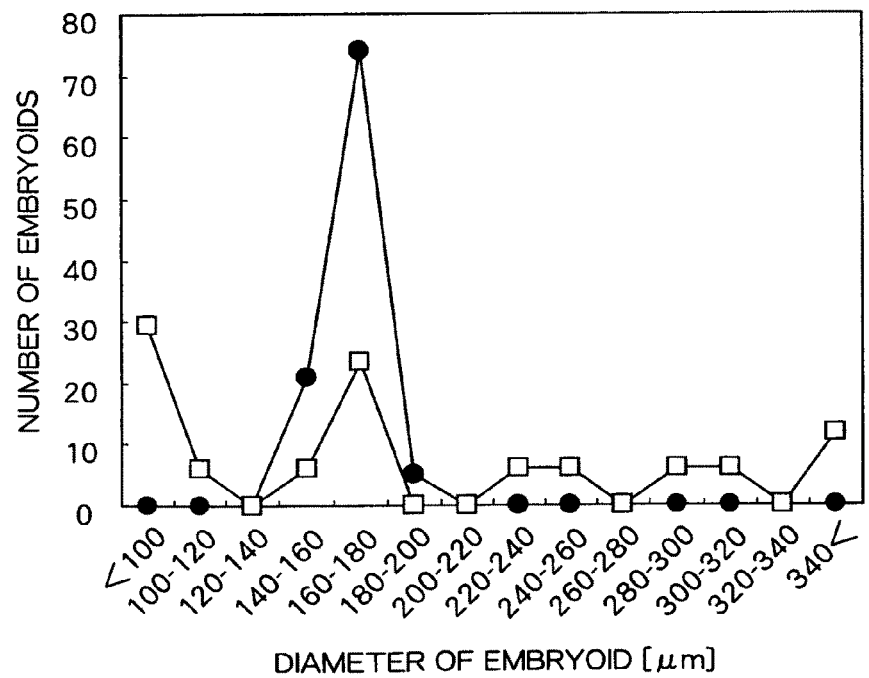
FIG. 32 is an explanatory view illustrating another example of the particle size distribution of the embryoids formed in the cell culture instrument according to the embodiment of the present invention.

FIG. 31 represents the distribution of the diameter of the hepatocyte spheroids formed in the respective microwells 21 of the instrument 1 or the respective control culture dishes on the fifth day of the culture. FIG. 32 represents the distribution of the diameter of the embryoids formed in the respective microwells 21 of the instrument 1 or the respective control culture dishes on the fifth day of the culture. In each of FIGS. 31 and 32, the horizontal axis represents the diameter (μm) of the cell organoid and the vertical axis represents the number (N) of the cell organoids of the respective diameters. In addition, the closed circle symbol represents a measured value for the cell organoid formed in the microwell group 20 of the instrument 1. The opened square symbol represents a measured value for the cell organoid formed in the control culture dish. As illustrated in FIGS. 31 and 32, cell organoids of various diameters were formed in the control culture dish. In contrast, cell organoids of uniform diameter were formed in the microwell group 20 of the instrument 1. In other words, by culturing the primary rat hepatocytes in the microwell group 20 of the instrument 1, one hepatocyte spheroid with diameters in the range of 120 μm to 200 μm was formed in each of the microwells 21, while being adhered near the center of the bottom 22. In addition, by culturing the mouse ES cells in the microwell group 20 of the instrument 1, one embryoid with diameters in the range of 120 μm to 200 μm was formed in each of the microwells 21, while being adhered near the center of the bottom 22.

EXAMPLE 6

An instrument 1 in which four macrowells 50a to 50d were formed as illustrated in FIGS. 6 to 9 was produced. Then, it was confirmed that those four macrowells 50a to 50d could keep solutions independently from one another. That is, in a manner similar to that of the above-mentioned example 1, 378 circular microwells 21 of 300 μm in diameter, 200 μm in depth, and 330 μm in center distance were formed in each of four rectangular areas (6 mm×6 mm) spaced apart from one other on the surface of a flat plate (24 mm×24 mm, 700 μm in thickness) formed of PMMA, thereby producing a base member 2 in which four macrowell groups 20a to 20d were formed as illustrated in FIGS. 6 to 9.

On the other hand, rectangular through-holes (7 mm×7 mm) were formed in a flat plate (24 mm×24 mm, 3 mm in thickness) formed of PDMS. Each of the rectangular through-holes could house one of four macrowell groups 20a to 20d of the first substrate portion 10 so as to be different from one another, thereby producing a frame member 30 in which four window portions 40a to 40d were formed as illustrated in FIGS. 6 to 9.

Figure 33:
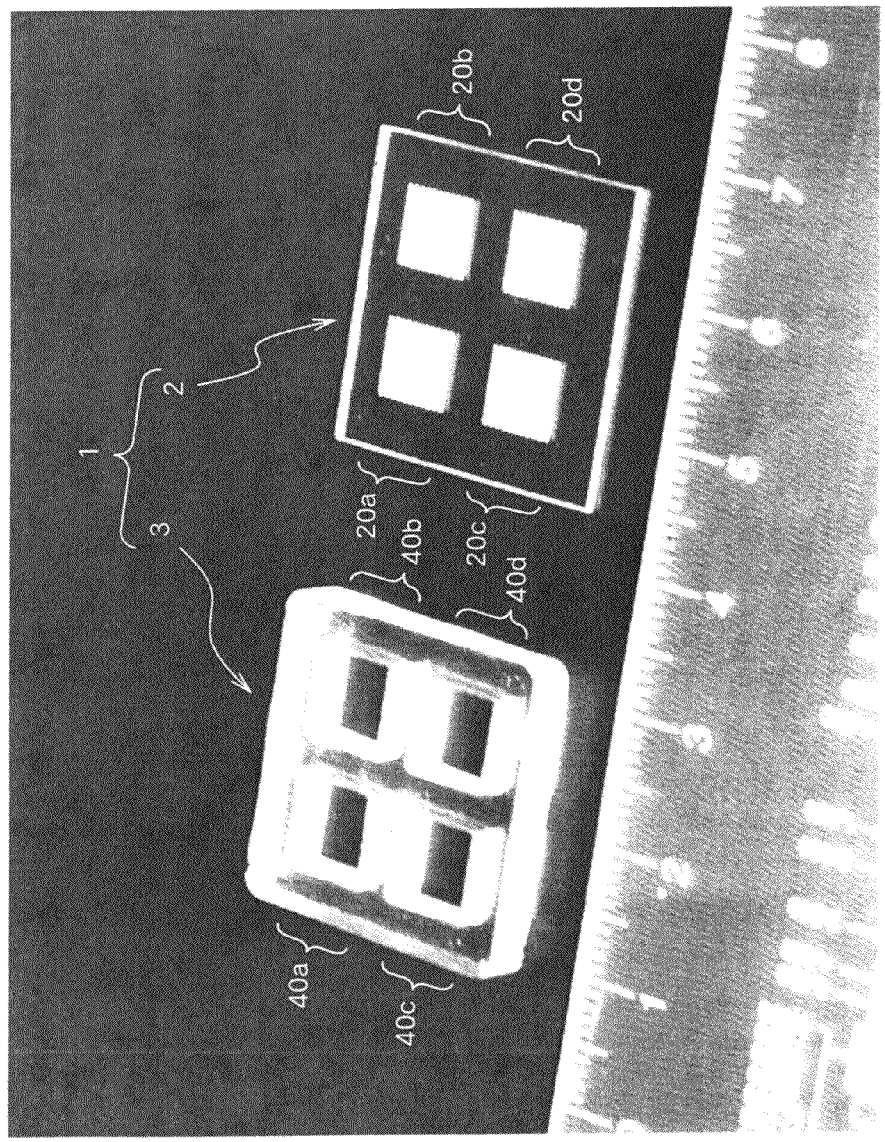
FIG. 33 is a photograph showing an example of an external appearance of a separated state of the cell culture instrument according to the embodiment of the present invention.
Figure 34:
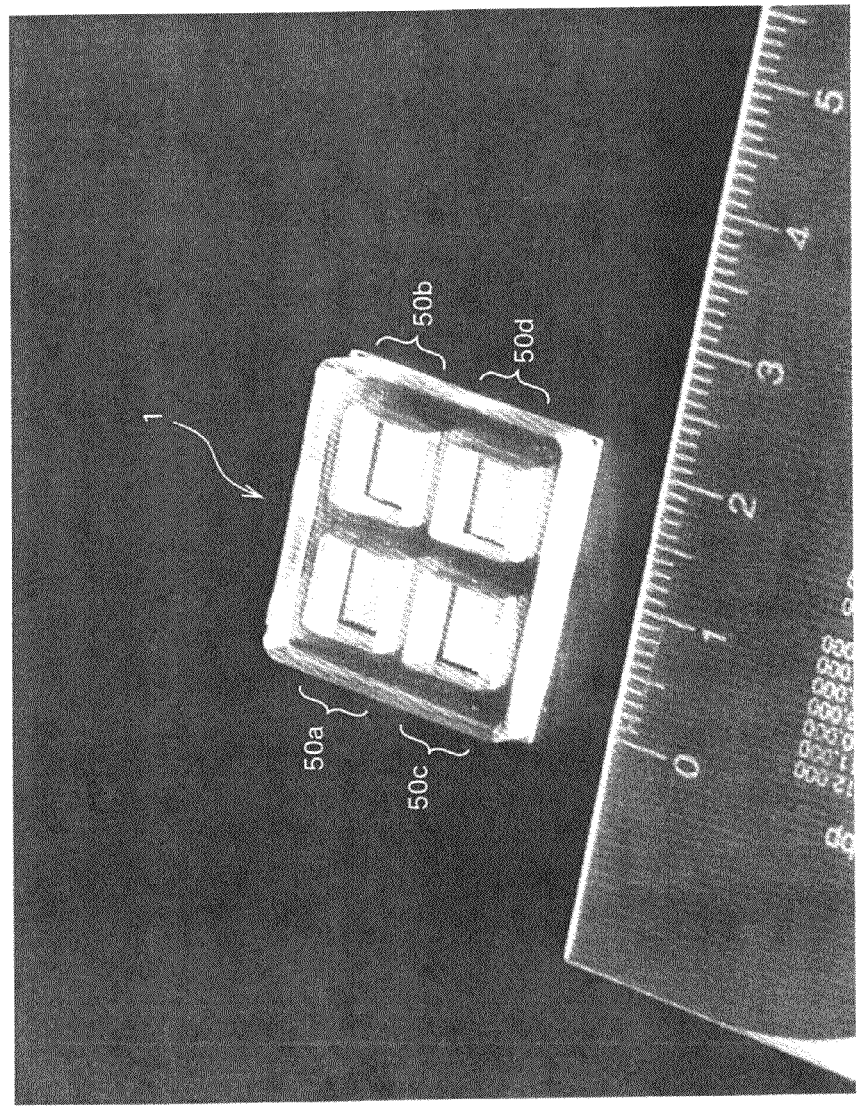
FIG. 34 is a photograph showing an example of an external appearance of an attached state of the cell culture instrument according to the embodiment of the present invention.
Figure 35:
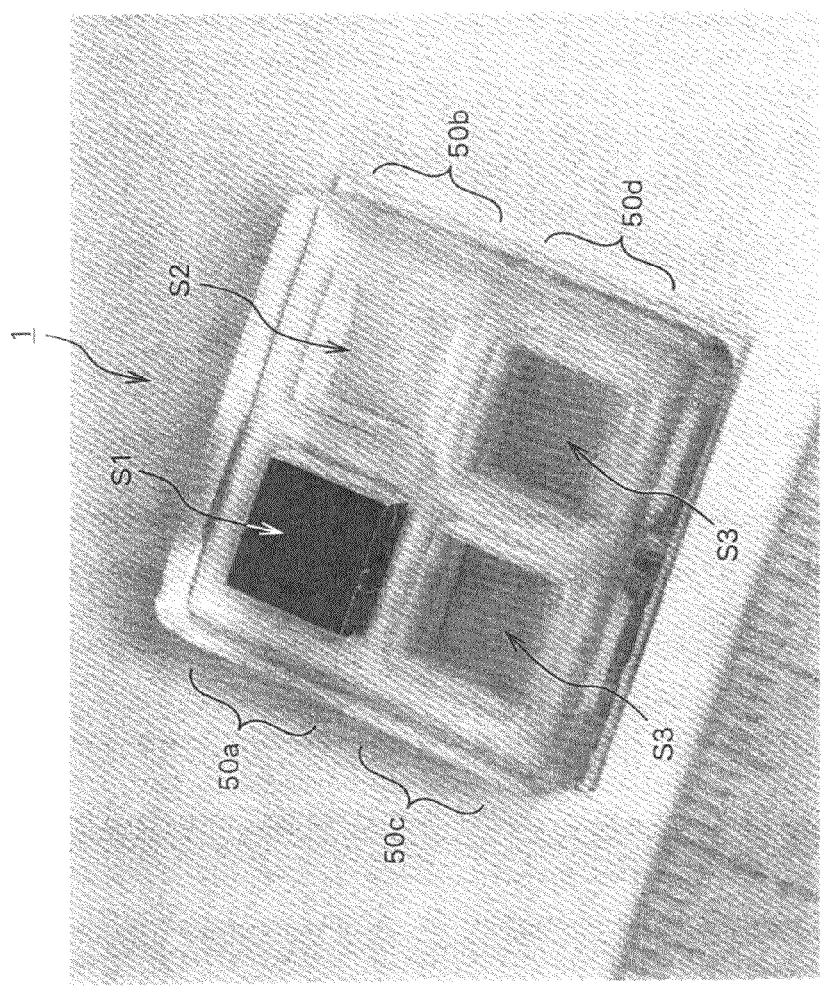
FIG. 35 is a photograph showing another example of the external appearance of a separated state of the cell culture instrument according to another embodiment of the present invention.

FIG. 33 represents a photograph of the instrument 1 in a state that the base member 2 and the frame member 3 are being detached from each other with four microwell groups 20a to 20d being formed in the base member 2, and four window portions 40a to 40d being formed in the frame member 3. In addition, FIG. 34 represents a photograph of the instrument 1 in a state that the base member 2 and the frame member 3 are attached to each other, thereby forming four macrowells 50a to 50d. FIG. 35 represents a photograph of the instrument 1 in an attached state, where different solutions are held in each of four macrowells 50a to 50d. That is, in the instrument 1 illustrated in FIG. 35, the first macrowell 50a holds a dark blue-colored trypan blue solution S1 which can be used for determining whether the cells are viable or dead. The second macrowell 50b holds a transparent and colorless buffer S2. Each of the third macrowell 50c and the fourth macrowell 50d hold a red-colored culture medium S3 added with phenol red as a red pigment for pH determination. As illustrated in FIG. 35, it was confirmed that four macrowells 50a to 50d of the instrument 1 could hold the respective solutions independently from one another.

EXAMPLE 7

By using the instrument 1 produced in a manner similar to that of the above-mentioned example 1, the relationship between the distance D between the marginal well 21i and the frame member 3 illustrated in FIG. 5 and the size of cell organoids formed in each of the marginal well 21i and the central well 21ii was investigated.

In other words, five different instruments 1 were produced so that each of them includes a base member 2 formed of a flat plate (24 mm×24 mm, 400 μm in thickness) formed of PMMA and a frame member 3 formed of a flat plate (20 mm×20 mm, 1.1 mm in thickness) formed of PDMS, while having different values of the above-mentioned distance D.

Specifically, the base member 2 was produced so that 900 circular microwells 21 of 300 μm in diameter and 300 μm in depth were regularly arranged in the 10 mm×10 mm rectangular area of the upper surface 11. In other words, on the base member 2, there were 30 rows in parallel with one another at certain intervals, where each well included 30 microwells 21 arranged in line at certain intervals. The bottom 22 of each microwell 21 was made cellular non-adhesive.

On the other hand, five different frame members 3 were produced so that they had their own rectangular window portions 40 having different sizes, each having a distance D of 0 μm, 300 μm, 600 μm, 1000 μm, or 2000 μm when being attached to the base member 2. A combination of any one of those five different frame members 3 and the base member 2 allowed the production of five different instruments 1 each having one macrowell 50, while being different with respect to the distance D.

Next, each instrument 1 was placed in a plastic dish of 35 mm in diameter (tissue culture dish, manufactured by Becton, Dickinson and Company). Then, $2\times10^5$ HepG2 cells dispersed in a culture medium was inoculated in the macrowell 50 of each instrument 1. The culture medium was left for two hours in the macrowell 50 to culture the cells. Thus, the cells were allowed to sediment on the bottom 51 of the macrowell 50. After that, 2 mL of the culture medium was added to the plastic dish so that the entire instrument 1 was immersed in the culture medium. Subsequently, the cells were cultured for 14 days in the macrowell 50 of the instrument 1 being immersed in the culture medium. Further, another instrument 1 in a separated state was prepared such that it only included a base member 2 being detached from a frame member 3.

Then, HepG2 cells were inoculated so that the cell density per area of the microwell group 20 could be equal to that of the above-mentioned instrument 1 in an attached state, followed by being cultured in a similar manner. Consequently, one spherical cell organoid (HepG2 spheroid) was formed as a three-dimensional aggregate of the HepG2 cells in each microwell 21 of each instrument 1.

Then, for each of the instruments 1, phase contrast microscopic observation was carried out for measuring the diameter of a marginal organoid Ti formed in each of 50 wells of the marginal wells 21i in the marginal row of the microwell group 20, and the diameter of a central organoid Tii formed in each of 50 wells of the central wells 21ii in the 11th to 20th rows from the margin. Further, a ratio of an arithmetic average value of the diameter of the central organoid Tii and the arithmetic average value of the diameter of the marginal organoid Ti was calculated as a "diameter ratio".

FIG. 36 is a phase contrast micrograph representing cell organoids formed in six different instruments 1. FIG. 36(A) is a photograph of the instrument 1 with a distance D of 0 μm. FIG. 36(B) is a photograph of the instrument 1 with a distance D of 300 μm. FIG. 36(C) is a photograph of the instrument 1 with a distance D of 600 μm. FIG. 36(D) is a photograph of the instrument 1 with a distance D of 1000 μm. FIG. 36(E) is a photograph of the instrument 1 with a distance D of 2000 μm. FIG. 36(F) is a photograph of the instrument 1 without the frame member 3. The length of the scale bar on the lower side of FIG. 36(F) represents 500 μm.

As illustrated in FIG. 36, in the bottom 51 of the macrowell 50 of each instrument 1, one spherical marginal organoid Ti was formed in each of the marginal wells 21i adjacent to the frame member 3. One spherical central organoid Tii was formed in each of the central wells 21ii located on the inner side. The marginal organoid Ti and the central organoid Tii remained suspended without being adhered on the bottom 22 and the inner wall 23 in the marginal well 21i and the central well 21ii, respectively. It should be noted that in Example 7, clear microphotographs could be obtained as illustrated in FIG. 36 by sufficiently immersing the entire instrument 1 in the culture medium and improving the operation conditions of a microscope, such as appropriately adjusting the strength of light at the time of microscopic observation.

FIG. 37 illustrates a diameter ratio of cell organoids calculated for each instrument 1. In FIG. 37, the horizontal axis represents the distance D of each instrument 1 and the vertical axis represents a diameter ratio in each instrument 1. It should be noted that, the sign "no frame member" on the right end of the horizontal axis in FIG. 37 represents a result obtained using the base member 2 being detached from the frame member 3.

As illustrated in FIG. 37, a decrease in diameter ratio could be attained by reducing the distance D, compared with the case that the frame member 3 was being detached ("no frame member"). In other words, a distance D of 2000 μm or less could result in a diameter ratio of 1.20 or less. In addition, a distance D of 1000 μm or less could result in a diameter ratio of 1.16 or less. In particular, when the distance D was reduced to 600 μm or less, the diameter ratio could be reduced to 1.15 or less.

Therefore, in the formation of cell organoids using the instrument 1, it was confirmed that variations in size of marginal organoids and central organoids could be effectively reduced and a large number of cell organoids of extremely uniform size could be easily and reliably obtained by restricting the distance D of the instrument 1 within a predetermined minute range.

It should be noted that the instrument 1 according to the present invention and the cell culture method using the same are not limited to those of the above-mentioned Examples. For example, the microwell 21 of the base member 2 may be of any shape for different purposes. In other words, the opening portion 24 and the bottom 22 of the microwell 2 are not limited to be circular, and they may be formed in, for example, a polygonal shape. In addition, the opening portion 24 and the bottom 22 may have their own shapes different from each other. Further, the opening portion 24 and the bottom 22 may be formed having different surface areas. In other words, for example, the inner wall 23 of the microwell 21 may be obliquely formed to make the area of the bottom 22 smaller than that of the opening portion 24. In addition, the microwell 21 may be formed into a taper shape so that it is substantially free of a bottom 22 and only provided with an inclined inner wall 23. In addition, the window portion 40 of the frame member 3 may be formed in any shape for different purposes, such as a circular or polygonal shape.

Further, if a plurality of microwell groups 20 is formed in the base member 2, an arbitrary number; such as one or a plurality, of window portions 40 may be formed in the frame member 3. In addition, in the culture process using the instrument 1, one base member 2 may be used in combination with a plurality of different frame members 3. In other words, for example, the base member 2 in which a predetermined number of microwell groups 20 is formed may be used, if required, in combination with each of a plurality of frame members 3 each having different numbers of window portions 40. Specifically, if four microwell groups 20a to 20d are formed in the base member 2 as illustrated in FIGS. 6 to 9, in the inoculation step s100, the frame member 3 having four window portions 40a to 40d as illustrated in FIGS. 6 to 9 is attached to the base member 2 and cells are then inoculated into each of four microwell groups 20a to 20d. Then, in the culture step 3200, the culture of cells is continued in the instrument 1 in a separated state in which the frame member 3 is being removed as illustrated in FIG. 19. Further, in the treatment step s300, the frame member 3 having only one window portion 40 as illustrated in FIGS. 11 and 12 is attached to the base member 2. The composition of a solution which is brought into contact with cells in one macrowell group 20b corresponding to one macrowell 50 among the four microwell groups 20a to 20d may be different from the compositions of the respective solutions which are brought into contact with the cells in other three macrowell groups 20a, 20c, and 20d.

In addition, the holding member 4 is not limited to one having abutting portions that abuts on the whole periphery 22 of the base member 2 and the whole periphery 33 of the frame member 3 as illustrated in FIGS. 15 to 17. In other words, the holding member 4 may have abutting portions that abut on part of each of the periphery 22 and the periphery 33 as long as they can temporarily hold the base member 2 and the frame member 3 in a predetermined positional relationship.

The invention claimed is:

1. A cell culture instrument, comprising:
    a base portion in which a well group including a plurality of first wells capable of holding cells is formed; and
    a frame portion vertically arranged on an upper surface of the base portion around the well group of the base portion to form a second well being capable of holding a solution, wherein:
        the base portion consists of a base member, the frame portion consists of a frame member, and the base member and the frame member are formed independently from each other;
        the frame member is provided with a through-hole that corresponds to the well group and is constituted so as to be attached to and detached from the base member;
        in a state that the frame member is being attached to the base member, an inner wall of the through-hole is vertically arranged around the well group to form the second well;
        a first joint portion and a second joint portion which: i) are configured to be connected to each other, and ii) are formed at corresponding positions on the base member and the frame member, respectively;
        a plurality of the well groups are formed apart from each other in the base member;
        the first joint portion is formed around and completely encircles all of the plurality of the well groups.

2. The cell culture instrument according to claim 1, wherein an opening portion of the first well has an area in a range of 100 to $1\times10^6$ μm².

3. The cell culture instrument according to claim 1, wherein:
    a plurality of well groups are formed apart from each other on the base member; and
    at least one through-hole that corresponds to one of the plurality of the well groups is formed in the frame member.

4. The cell culture instrument according to claim 3, wherein:
    a plurality of the through-holes, each of which corresponds to one of the plurality of the well groups, are formed in the frame member; and
    in a state that the frame member is being attached to the base member, the inner wall of each of the plurality of the through-holes is vertically arranged around one of the corresponding well groups to form a plurality of second wells.

5. The cell culture instrument according to claim 1, wherein
    one of the first joint portion and the second joint portion is formed in a convex shape and the other thereof is formed in a concave shape so that the first joint portion and the second joint portion can be fit together.

6. The cell culture instrument according to claim 1, further comprising a holding member, wherein
    the holding member integrally holds the base member and the frame member attached to the base member and includes an abutting portion that fixes a relative position between the base member and the frame member by abutting on at least part of the periphery of each of the base member and the frame member.

7. A frame member for a cell culture instrument which is constituted so as to be attachable to and detachable from a base member having a well group comprising:
    a plurality of first wells capable of holding cells, in which a through-hole corresponding to the well group is formed, the frame member being configured to be attached to the base member so that an inner wall of the through-hole is vertically arranged on an upper surface of the base portion around the well group to form a second well capable of holding a solution and the frame member is to be detached from the base member thereafter;
    a first joint portion and a second joint portion which: i) are configured to be connected to each other, and ii) are formed at corresponding positions on the base member and the frame member, respectively; wherein
    a plurality of the well groups are formed apart from each other in the base member; and the first joint portion is formed around and completely encircles all of the plurality of the well groups.

8. A cell culture method comprising the following steps:
providing a cell culture instrument wherein the cell culture instrument comprising:
a base portion in which a well group including a plurality of first wells capable of holding cells is formed; and
a frame portion vertically arranged on an upper surface of the base portion around the well group of the base portion to form a second well being capable of holding a solution, wherein
the base portion consists of a base member, the frame portion consists of a frame member, and the base member and the frame member are formed independently from each other;
the frame member is provided with a through-hole that corresponds to the well group and is constituted so as to be attached to and detached from the base member;
in a state that the frame member is being attached to the base member, an inner wall of the through-hole is vertically arranged around the well group to form the second well;
a first joint portion and a second joint portion which: i) are configured to be connected to each other, and ii) are formed at corresponding positions on the base member and the frame member, respectively;
a plurality of the well groups are formed apart from each other in the base member; and
the first joint portion is formed around and completely encircles all of the plurality of the well groups culturing cells in the cell culture instrument.

9. The cell culture method according to claim 8, comprising the steps of:
inoculating cells into one of the well groups corresponding to the second well by injecting a solution containing the cells in the second well of the cell culture instrument in a state that the frame member is attached to the base member; and
culturing the cells in the well group in a state that the frame member is removed from the base member.

10. The cell culture method according to claim 8, comprising the steps of:
culturing cells in the well group; and
bringing the cells in one well group corresponding to the second well into contact with a predetermined solution by injecting the predetermined solution into the second well of the cell culture instrument in a state that the frame member is being attached to the base member.

11. The cell culture method according to claim 8, wherein:
a plurality of the through-holes, each of which corresponds to one of the plurality of well groups, are formed in the frame member; and
in a state that the frame member is being attached to the base member, an inner wall of each of the plurality of the through-holes is vertically arranged around one of the corresponding well groups to form a plurality of second wells,
the cell culture method comprising the steps of:
culturing cells in the plurality of the well groups; and
bringing the cells in the plurality of the well groups corresponding to the plurality of the second wells into contact with solutions different from one another by injecting the solutions different from one another into the plurality of the second wells of the cell culture instrument in a state that the frame member is being attached to the base member.

12. The cell culture instrument according to claim 1, wherein the first joint portion is formed around and completely encircles each of the plurality of the well groups.

13. The cell culture instrument according to claim 1, wherein the frame member comprises a handle that is configured to be pinched by an operator.

14. The cell culture instrument according to claim 1, further comprising:
a holding member having a housing portion where an inner wall is formed, so that a periphery of the base member and a periphery of the frame member, that is attached to the base member, abut the inner wall.

15. The cell culture instrument according to claim 1, wherein the frame member is provided with at least one through-hole that corresponds to only a part of the plurality of the well groups.

16. A cell culture instrument, comprising:
a base portion in which a well group including a plurality of first wells capable of holding cells is formed; and
a frame portion vertically arranged on an upper surface of the base portion around the well group of the base portion to form a second well being capable of holding a solution, wherein:
the base portion consists of a base member, the frame portion consists of a frame member, and the base member and the frame member are formed independently from each other;
the frame member is provided with a through-hole that corresponds to the well group and is constituted so as to be attached to and detached from the base member;
in a state that the frame member is being attached to the base member, an inner wall of the through-hole is vertically arranged around the well group to form the second well;
a first joint portion and a second joint portion which: i) are configured to be connected to each other, and ii) are formed at corresponding positions on the base member and the frame member, respectively;
a plurality of the well groups and a plurality of first joint portions are formed apart from each other in the base member;
the first joint portion is formed around each of the plurality of the well groups; and
the plurality of first joint portions are interdisposed between each of the plurality of well groups.

17. The cell culture instrument according to claim 16, wherein
the first joint portion defines a protrusion extending substantially perpendicular to the base member.

18. The cell culture instrument according to claim 16, wherein the frame member comprises a handle that is configured to be pinched by an operator.

19. The cell culture instrument according to claim 16, further comprising:
a holding member having a housing portion where an inner wall is formed, so that a periphery of the base member and a periphery of the frame member, that is attached to the base member, abut the inner wall.

20. The cell culture instrument according to claim 16, wherein the frame member is provided with at least one through-hole that corresponds to only a part of the plurality of the well groups.

21. A cell culture method comprising the following steps:
providing a cell culture instrument wherein the cell culture instrument comprising:
a base portion in which a well group including a plurality of first wells capable of holding cells is formed; and a frame portion vertically arranged on an upper surface of the base portion around the well group of the base portion to form a second well being capable of holding a solution, wherein:

the base portion consists of a base member, the frame portion consists of a frame member, and the base member and the frame member are formed independently from each other;

the frame member is provided with a through-hole that corresponds to the well group and is constituted so as to be attached to and detached from the base member;

in a state that the frame member is being attached to the base member, an inner wall of the through-hole is vertically arranged around the well group to form the second well;

a first joint portion and a second joint portion which: i) are configured to be connected to each other, and ii) are formed at corresponding positions on the base member and the frame member, respectively;

a plurality of the well groups and a plurality of first joint portions are formed apart from each other in the base member;

the first joint portion is formed around each of the plurality of the well groups; and the plurality of first joint portions are interdisposed between each of the plurality of well groups culturing cells in the cell culture instrument.

* * * * *